(12) United States Patent
Jin et al.

(10) Patent No.: US 11,898,678 B2
(45) Date of Patent: *Feb. 13, 2024

(54) SELF-CLOSING BAG CONNECTOR

(71) Applicant: CONVATEC TECHNOLOGIES INC., Las Vegas, NV (US)

(72) Inventors: Yun Jin, Bedminster, NJ (US); Bret Weig, Browns Mills, NJ (US); John Cline, New Brunswick, NJ (US); Mingliang Lawrence Tsai, Holmdel, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 241 days.

This patent is subject to a terminal disclaimer.

(21) Appl. No.: 17/538,160

(22) Filed: Nov. 30, 2021

(65) Prior Publication Data
US 2022/0090720 A1 Mar. 24, 2022

Related U.S. Application Data

(63) Continuation of application No. 16/718,166, filed on Dec. 17, 2019, now Pat. No. 11,187,364, which is a
(Continued)

(51) Int. Cl.
*A61M 39/10* (2006.01)
*F16L 37/38* (2006.01)
(Continued)

(52) U.S. Cl.
CPC ............ *F16L 37/32* (2013.01); *A61F 5/4405* (2013.01); *A61M 39/1011* (2013.01);
(Continued)

(58) Field of Classification Search
CPC . F16L 37/32; F16L 37/38; F16L 37/46; F16L 37/40; F16L 37/367; A61F 5/4405;
(Continued)

(56) References Cited

U.S. PATENT DOCUMENTS

| 3,446,245 A | 5/1969 | Snyder, Jr. |
| 3,529,599 A | 9/1970 | Folkman et al. |

(Continued)

FOREIGN PATENT DOCUMENTS

| EP | 3001976 A1 | 4/2016 |
| EP | 3100758 A1 | 12/2016 |

(Continued)

OTHER PUBLICATIONS

Communication Pursuant to Article 94(3) EPC; European Patent Office; European Application No. 14832561T8.1; dated May 25, 2020; 4 pages.

*Primary Examiner* — John Bastianelli
(74) *Attorney, Agent, or Firm* — Taft Stettinius & Hollister LLP; Ryan O. White; Derek B. Lavender

(57) ABSTRACT

A bag connector system includes a first coupling element, with a self-closing seal and a housing having a fluid inlet port and a fluid outlet port, and a second coupling element, with a housing having a fluid inlet end and a fluid outlet end. The fluid inlet end is configured to displace the self-closing seal when inserted into the fluid outlet port of the first coupling element. A bag connector system optionally includes a locking mechanism to maintain the first coupling element and second coupling element in a coupled state. Uncoupling of the first and second coupling elements results in minimal fluid contamination on the outer surfaces of the coupling elements. The bag connector systems provided herein are included in medical appliances for waste management.

20 Claims, 19 Drawing Sheets

Related U.S. Application Data continuation of application No. 15/495,712, filed on Apr. 24, 2017, now Pat. No. 10,507,318, which is a continuation of application No. 14/449,035, filed on Jul. 31, 2014, now Pat. No. 9,669,205.

(60) Provisional application No. 61/929,923, filed on Jan. 21, 2014, provisional application No. 61/861,357, filed on Aug. 1, 2013.

(51) Int. Cl.
*F16L 37/32* (2006.01)
*A61M 39/26* (2006.01)
*A61F 5/44* (2006.01)
*F16L 37/46* (2006.01)

(52) U.S. Cl.
CPC .............. *A61M 39/26* (2013.01); *A61M 39/10* (2013.01); *A61M 2039/263* (2013.01); *F16L 37/38* (2013.01); *F16L 37/46* (2013.01); *Y10T 137/9029* (2015.04)

(58) Field of Classification Search
CPC .. A61M 39/1011; A61M 39/26; A61M 39/10; A61M 2039/263; Y10T 137/9029; Y10T 137/87949; Y10T 137/87957
USPC .......... 137/614.03, 614.04; 251/149.1, 149.6
See application file for complete search history.

(56) References Cited

U.S. PATENT DOCUMENTS

| | | |
|---|---|---|
| 4,629,159 A | 12/1986 | Wellenstam |
| 4,828,554 A | 5/1989 | Griffin |
| 5,350,364 A | 9/1994 | Stephens et al. |
| 5,482,083 A | 1/1996 | Jenski |
| 5,496,300 A | 3/1996 | Hirsch et al. |
| 5,609,195 A | 3/1997 | Stricklin et al. |
| 5,848,997 A | 12/1998 | Erskine et al. |
| 7,537,024 B2 | 5/2009 | Adams et al. |
| 9,669,205 B2 | 6/2017 | Jin et al. |
| 10,207,076 B2 | 2/2019 | Foley et al. |
| 10,426,584 B2 | 10/2019 | McClurg |
| 10,426,654 B2 | 10/2019 | Ugarte |
| 10,426,918 B2 | 10/2019 | Foley et al. |
| 10,426,919 B2 | 10/2019 | Erbey et al. |
| 10,434,282 B2 | 10/2019 | Kearns et al. |
| 10,441,454 B2 | 10/2019 | Tanghoej et al. |
| 10,449,083 B2 | 10/2019 | Pierson |
| 10,449,327 B2 | 10/2019 | Overtoom |
| 10,449,328 B2 | 10/2019 | Tanghoej et al. |
| 10,449,329 B2 | 10/2019 | Foley et al. |
| 10,463,466 B2 | 11/2019 | Cullison |
| 10,463,833 B2 | 11/2019 | Clarke et al. |
| 10,470,861 B2 | 11/2019 | Khamis et al. |
| 10,485,483 B1 | 11/2019 | Brody |
| 10,485,644 B2 | 11/2019 | Orr et al. |
| 10,493,230 B2 | 12/2019 | Guldager et al. |
| 10,493,231 B2 | 12/2019 | McMenamin et al. |
| 10,493,252 B2 | 12/2019 | Browne et al. |
| 10,506,965 B2 | 12/2019 | Cooper et al. |
| 10,507,318 B2 | 12/2019 | Jin et al. |
| 10,512,713 B2 | 12/2019 | Erbey et al. |
| 10,531,894 B2 | 1/2020 | Connors et al. |
| 10,531,976 B2 | 1/2020 | Palmer |
| 10,548,523 B2 | 2/2020 | Admadi et al. |
| 10,569,046 B2 | 2/2020 | Steindahl et al. |
| 10,569,047 B2 | 2/2020 | Farrell et al. |
| 10,569,051 B2 | 2/2020 | Conway et al. |
| 10,575,935 B2 | 3/2020 | Wei et al. |
| 10,588,774 B2 | 3/2020 | Alhaqqan |
| 10,589,061 B2 | 3/2020 | Palmer |
| 10,589,093 B2 | 3/2020 | Imran |
| 10,610,344 B2 | 4/2020 | Shapiro et al. |
| 10,610,664 B2 | 4/2020 | Erbey, II et al. |
| 10,617,843 B2 | 4/2020 | Paz |
| 10,631,788 B2 | 4/2020 | Brody |
| 10,639,451 B2 | 5/2020 | Kearns et al. |
| 10,639,452 B2 | 5/2020 | Linares et al. |
| 10,646,688 B2 | 5/2020 | Hannon et al. |
| 10,667,894 B2 | 6/2020 | Forsell |
| 10,668,249 B2 | 6/2020 | Douglas et al. |
| 10,675,134 B2 | 6/2020 | Herrera et al. |
| 10,675,435 B2 | 6/2020 | Herrera et al. |
| 10,682,214 B2 | 6/2020 | Sufyan et al. |
| 10,690,655 B2 | 6/2020 | Duval |
| 10,702,671 B2 | 7/2020 | Terry |
| 10,709,819 B2 | 7/2020 | Littleton et al. |
| D893,706 S | 8/2020 | Lessmann |
| 10,736,491 B2 | 8/2020 | Truckai |
| 10,737,057 B1 | 8/2020 | Mikhail et al. |
| 10,744,298 B1 | 8/2020 | Bello et al. |
| 10,751,493 B2 | 8/2020 | Gregory et al. |
| 10,758,704 B2 | 9/2020 | Hickmott et al. |
| 10,765,833 B2 | 9/2020 | Kearns |
| 10,765,834 B2 | 9/2020 | Erbey, II et al. |
| 10,772,755 B2 | 9/2020 | Gregory |
| 10,780,243 B2 | 9/2020 | Reyes |
| 10,780,244 B2 | 9/2020 | Conway et al. |
| 10,780,245 B2 | 9/2020 | Schonfeldt |
| 10,799,687 B1 | 10/2020 | Scott |
| 10,807,287 B2 | 10/2020 | Rolsted et al. |
| 10,814,097 B2 | 10/2020 | Palmer |
| 2003/0018293 A1 | 1/2003 | Tanghoj et al. |
| 2004/0176703 A1 | 9/2004 | Christensen et al. |
| 2005/0043715 A1 | 2/2005 | Nestenborg et al. |
| 2005/0101939 A1 | 5/2005 | Mitchell |
| 2006/0163097 A1 | 7/2006 | Murray et al. |
| 2009/0137985 A1 | 5/2009 | Tanghoej et al. |
| 2010/0324535 A1 | 12/2010 | Triel |
| 2011/0190736 A1 | 8/2011 | Young et al. |
| 2011/0224653 A1 | 9/2011 | Torstensen |
| 2013/0138135 A1 | 5/2013 | Rosen et al. |
| 2013/0161208 A1 | 6/2013 | Gustavsson |
| 2013/0161227 A1 | 6/2013 | Gustavsson |
| 2013/0261608 A1 | 10/2013 | Tanghoj |
| 2014/0066905 A1 | 3/2014 | Young |
| 2014/0288517 A1 | 9/2014 | Tsai et al. |
| 2014/0336569 A1 | 11/2014 | Gobel |
| 2014/0378951 A1 | 12/2014 | Dye |
| 2015/0133898 A1 | 5/2015 | Murray et al. |
| 2015/0273180 A1 | 10/2015 | Schonfeldt |
| 2015/0273747 A1 | 10/2015 | Montes de Oca Balderas et al. |
| 2015/0290421 A1 | 10/2015 | Glickman et al. |
| 2015/0297862 A1 | 10/2015 | Sadik et al. |
| 2015/0320970 A1 | 11/2015 | Foley et al. |
| 2016/0067445 A1 | 3/2016 | Murray et al. |
| 2016/0184551 A1 | 6/2016 | Nyman et al. |
| 2016/0206469 A1 | 7/2016 | Prezelin |
| 2016/0287759 A1 | 10/2016 | Clarke et al. |
| 2016/0317715 A1 | 11/2016 | Rostami et al. |
| 2016/0325903 A1 | 11/2016 | Doerschner et al. |
| 2017/0000978 A1 | 1/2017 | Murray et al. |
| 2017/0021128 A1 | 1/2017 | Erbey, II et al. |
| 2017/0105826 A1 | 4/2017 | Erikstrup |
| 2017/0348137 A1 | 12/2017 | Hvid et al. |
| 2017/0348138 A1 | 12/2017 | Hvid et al. |
| 2018/0015250 A1 | 1/2018 | Tsukada et al. |
| 2018/0021481 A1 | 1/2018 | Yin et al. |
| 2018/0050173 A1 | 2/2018 | Kearns |
| 2018/0071482 A1 | 3/2018 | Fitzpatrick et al. |
| 2018/0369474 A1 | 12/2018 | Falleboe et al. |
| 2019/0099583 A1 | 4/2019 | Charlez et al. |
| 2019/0224402 A1 | 7/2019 | Henry et al. |
| 2019/0240060 A1 | 8/2019 | He et al. |
| 2019/0247549 A1 | 8/2019 | Nielsen |
| 2019/0314044 A1 | 10/2019 | Long et al. |
| 2019/0314188 A1 | 10/2019 | Barrientos |
| 2019/0314190 A1 | 10/2019 | Sanchez et al. |
| 2019/0321587 A1 | 10/2019 | McMenamin et al. |
| 2019/0321589 A1 | 10/2019 | Bonneau |
| 2019/0358075 A1 | 11/2019 | Scharich, III et al. |
| 2019/0358435 A1 | 11/2019 | Andersin et al. |

(56) References Cited

U.S. PATENT DOCUMENTS

| | | |
|---|---|---|
| 2019/0365561 A1 | 12/2019 | Newton et al. |
| 2019/0366038 A1 | 12/2019 | Denman et al. |
| 2019/0374324 A1 | 12/2019 | Luleci |
| 2019/0381291 A1 | 12/2019 | Feld |
| 2019/0388659 A1 | 12/2019 | Ruel |
| 2020/0001045 A1 | 1/2020 | McIntyre |
| 2020/0001049 A1 | 1/2020 | House |
| 2020/0016380 A1 | 1/2020 | Murray et al. |
| 2020/0022636 A1 | 1/2020 | Suehara et al. |
| 2020/0030135 A1 | 1/2020 | Woodyard |
| 2020/0030582 A1 | 1/2020 | Dong |
| 2020/0030595 A1 | 1/2020 | Boukidjian et al. |
| 2020/0037832 A1 | 2/2020 | Wang et al. |
| 2020/0054800 A1 | 2/2020 | Wilbourn et al. |
| 2020/0094017 A1 | 3/2020 | Erbey, II et al. |
| 2020/0101280 A1 | 4/2020 | Peddicord |
| 2020/0129731 A1 | 4/2020 | Brar et al. |
| 2020/0139109 A1 | 5/2020 | Imran |
| 2020/0146799 A1 | 5/2020 | Connors et al. |
| 2020/0146871 A1 | 5/2020 | Palmer |
| 2020/0163543 A1 | 5/2020 | Schutt et al. |
| 2020/0163699 A1 | 5/2020 | Bacich et al. |
| 2020/0179644 A1 | 6/2020 | Guldbaek |
| 2020/0179665 A1 | 6/2020 | Orr et al. |
| 2020/0188631 A1 | 6/2020 | Hannon et al. |
| 2020/0206389 A1 | 7/2020 | Vange |
| 2020/0206411 A1 | 7/2020 | Henry et al. |
| 2020/0206468 A1 | 7/2020 | Olson et al. |
| 2020/0206470 A1 | 7/2020 | Orr et al. |
| 2020/0214820 A1 | 7/2020 | Bunch et al. |
| 2020/0215303 A1 | 7/2020 | Erbey, II et al. |
| 2020/0222188 A1 | 7/2020 | Smith et al. |
| 2020/0222220 A1 | 7/2020 | Kappus et al. |
| 2020/0222659 A1 | 7/2020 | Schertiger et al. |
| 2020/0222660 A1 | 7/2020 | Erbey et al. |
| 2020/0222674 A1 | 7/2020 | Inoue et al. |
| 2020/0229964 A1 | 7/2020 | Staali et al. |
| 2020/0230349 A1 | 7/2020 | McMenamin et al. |
| 2020/0230356 A1 | 7/2020 | Utas et al. |
| 2020/0230382 A1 | 7/2020 | Siebert |
| 2020/0238048 A1 | 7/2020 | Palmer |
| 2020/0246587 A1 | 8/2020 | Tal et al. |
| 2020/0246589 A1 | 8/2020 | Starr |
| 2020/0246594 A1 | 8/2020 | Miller |
| 2020/0254215 A1 | 8/2020 | Portela et al. |
| 2020/0261692 A1 | 8/2020 | Palmer |
| 2020/0262868 A1 | 8/2020 | Ricca et al. |
| 2020/0268947 A1 | 8/2020 | Erbey, II et al. |
| 2020/0276046 A1 | 9/2020 | Staali et al. |
| 2020/0276410 A1 | 9/2020 | Son |
| 2020/0281760 A1 | 9/2020 | Fleming |
| 2020/0282092 A1 | 9/2020 | Paul et al. |
| 2020/0306502 A1 | 10/2020 | Luning et al. |
| 2020/0315445 A1 | 10/2020 | Cheng et al. |
| 2020/0324006 A1 | 10/2020 | Paul et al. |
| 2020/0330724 A1 | 10/2020 | Mikhail et al. |

FOREIGN PATENT DOCUMENTS

| | | |
|---|---|---|
| EP | 3315159 A1 | 5/2018 |
| EP | 3351208 A1 | 7/2018 |
| JP | 61-192991 A | 8/1986 |
| JP | 9-327519 A | 12/1997 |
| JP | 9-512892 A | 12/1997 |
| JP | 2013-154252 A | 8/2013 |
| WO | 9530856 A1 | 11/1995 |
| WO | 2009048375 A1 | 4/2009 |
| WO | 2018134591 A1 | 7/2018 |
| WO | 2018143487 A1 | 8/2018 |
| WO | 2019014344 A1 | 1/2019 |
| WO | 2019038732 A1 | 2/2019 |
| WO | 2019038734 A1 | 2/2019 |
| WO | 2019106581 A1 | 6/2019 |
| WO | 2019123004 A1 | 6/2019 |
| WO | 2019184222 A1 | 10/2019 |
| WO | 2019222644 A1 | 11/2019 |
| WO | 2019229597 A1 | 12/2019 |
| WO | 2020015804 A1 | 1/2020 |
| WO | 2020093698 A1 | 5/2020 |
| WO | 2020110046 A1 | 6/2020 |
| WO | 2020110051 A1 | 6/2020 |
| WO | 2020132731 A1 | 7/2020 |
| WO | 2020136503 A1 | 7/2020 |
| WO | 2020136645 A1 | 7/2020 |
| WO | 2020144302 A1 | 7/2020 |
| WO | 2020160738 A1 | 8/2020 |
| WO | 2020173531 A1 | 9/2020 |
| WO | 2020173942 A1 | 9/2020 |
| WO | 2020178711 A1 | 9/2020 |
| WO | 20200214944 A1 | 10/2020 |

SELF-CLOSING BAG CONNECTOR

CROSS-REFERENCE

This application is a continuation of U.S. application Ser. No. 16/718,166, filed Dec. 17, 2019 and issued as U.S. Pat. No. 11,187,364 on Nov. 30, 2021, which is a continuation of U.S. application Ser. No. 15/495,712, filed Apr. 24, 2017 and issued as U.S. Pat. No. 10,507,318 on Dec. 17, 2019, which is a continuation of U.S. application Ser. No. 14/449,035, filed Jul. 31, 2014, and issued as U.S. Pat. No. 9,669,205 on Jun. 6, 2017, which claims benefit of U.S. Application Ser. No. 61/861,357, filed Aug. 1, 2013; and U.S. Application Ser. No. 61/929,923, filed Jan. 21, 2014, each of which is incorporated herein by reference in their entirety.

BACKGROUND OF THE INVENTION

Bag connector systems are used in a wide range of medical appliances to connect medical grade tubing to an external fluid collection bag. Such fluid is liquid or semi-liquid in nature, for example, containing particulates or other solid material. Collected fluid includes waste fluid, including liquid or semi-liquid feces, urine or other bodily fluid. It is desirable to design a bag connector system that is easy to use, manipulatable, and hygienic.

SUMMARY OF THE INVENTION

In one aspect, disclosed herein are bag connector systems comprising a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element; wherein uncoupling of the first coupling element and the second coupling element results in minimal fluid contamination on the outer surfaces of the coupling elements. In some embodiments, each of the first coupling element and the second coupling element further comprises a means to maintain the first coupling element and the second coupling element in a coupled state. In some embodiments, the self-closing seal is positioned within the housing of the first coupling element. In other embodiments, the self-closing seal is positioned outside of the housing of the first coupling element.

In some embodiments, the self-closing seal comprises a flapper connected to a leaf spring. In further embodiments, the housing of the first coupling element further comprises a washer. In some embodiments, each of the first coupling element and the second coupling element further comprises a means to maintain the first coupling element and the second coupling element in a coupled state. In further embodiments, the means to maintain the first coupling element and the second coupling element in a coupled state comprises a twist lock-in mechanism.

In some embodiments, the self-closing seal comprises a sliding cover connected to a spring element. In further embodiments, the housing of the first coupling element further comprises a washer. In some embodiments, the first coupling element further comprises at least one O-ring. In some embodiments, each of the first coupling element and the second coupling element further comprises a means to maintain the first coupling element and the second coupling element in a coupled state. In further embodiments, the means to maintain the first coupling element and the second coupling element in a coupled state comprises a cantilever snap-fit mechanism, including a single cantilever snap-fit mechanism. In other embodiments, the means to maintain the first coupling element and the second coupling element in a coupled state comprises a twist lock-in mechanism. In some embodiments, the second coupling element further comprises an O-ring positioned on the outer surface of the housing. In some embodiments, the second coupling element further comprises a check valve. In further embodiments, the check valve is a duckbill valve.

In some embodiments, the self-closing seal comprises a spring-loaded valve. In further embodiments, the spring-loaded valve comprises a spring seat, a spring element, and a flat cover. In still further embodiments, the spring-loaded valve is a poppet valve. In some embodiments, each of the first coupling element and the second coupling element further comprises a means to maintain the first coupling element and the second coupling element in a coupled state. In some embodiments, the second coupling element further comprises a sliding cover positioned over the fluid inlet port. In some embodiments, the second coupling element further comprises at least one O-ring. In some embodiments, each of the first coupling element and the second coupling element further comprises a means to maintain the first coupling element and the second coupling element in a coupled state. In further embodiments, the means to maintain the first coupling element and the second coupling element in a coupled state comprises a at least one cantilever snap, preferably a plurality of cantilever snaps, at the fluid outlet port of the first coupling element which forms a snap-fit with the sliding cover on the second coupling element.

In some embodiments, the self-closing seal between a first coupling element and second coupling element comprises a spring-loaded connector. In further embodiments, the first coupling element comprises a tube-connector base, a spring element, a sliding cover, at least one O-ring and a cap. In some embodiments, the tube-connector base comprises a fluid inlet port and a fluid outlet port. In other embodiments, the second coupling element comprises a bag connector base, a duckbill valve and a valve holder. In yet other embodiments, the bag-connector base comprises a fluid inlet port and a fluid outlet port. In some embodiments, when disconnected both connectors are in closed status, closing the drainage path within the first coupling element. In some embodiments, when connected the end of the valve holder within the second coupling element may push against the first flange of the sliding cover in the first coupling element until the side opening on the connector base of the first coupling element is exposed. In other embodiments, upon opening of the sliding cover in the first coupling element, the valve (optionally a duckbill valve) may be pushed open by the cap and base body of the second coupling element. Upon opening by the cap and base body of the second coupling element, the drainage path on both sides becomes open for drainage. In yet other embodiments, upon disconnection of the first coupling element and the second coupling element, the spring element may push the sliding cover of the first coupling element into position to close off the drainage path. Upon disconnection and closing of the drainage path, the duckbill valve may also remain closed.

In another aspect, disclosed herein are medical appliances comprising a fluid storage container and a bag connector system, the bag connector system comprising a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element; and wherein the fluid outlet end of the second coupling element is connected to the fluid storage container and uncoupling of the first coupling element and the second coupling element results in minimal fluid contamination on the outer surfaces of the coupling elements. In some embodiments, the self-closing seal is a flapper connected to a leaf spring, a sliding cover connected to a spring element, or a spring-loaded valve. In some embodiments, the second coupling element further comprises a check valve. In further embodiments, the check valve is a duckbill valve. In some embodiments, each of the first coupling element and the second coupling element further comprises a means to maintain the first coupling element and the second coupling element in a coupled state. In further embodiments, the means to maintain the first coupling element and the second coupling element in a coupled state is selected from a twist lock-in mechanism; a single cantilever snap-fit mechanism; and a cantilever snap-fit mechanism comprising a plurality of cantilever snaps at the fluid outlet port of the first coupling element which forms a snap-fit with the sliding cover on the second coupling element.

DETAILED DESCRIPTION OF THE INVENTION

Figure 1:
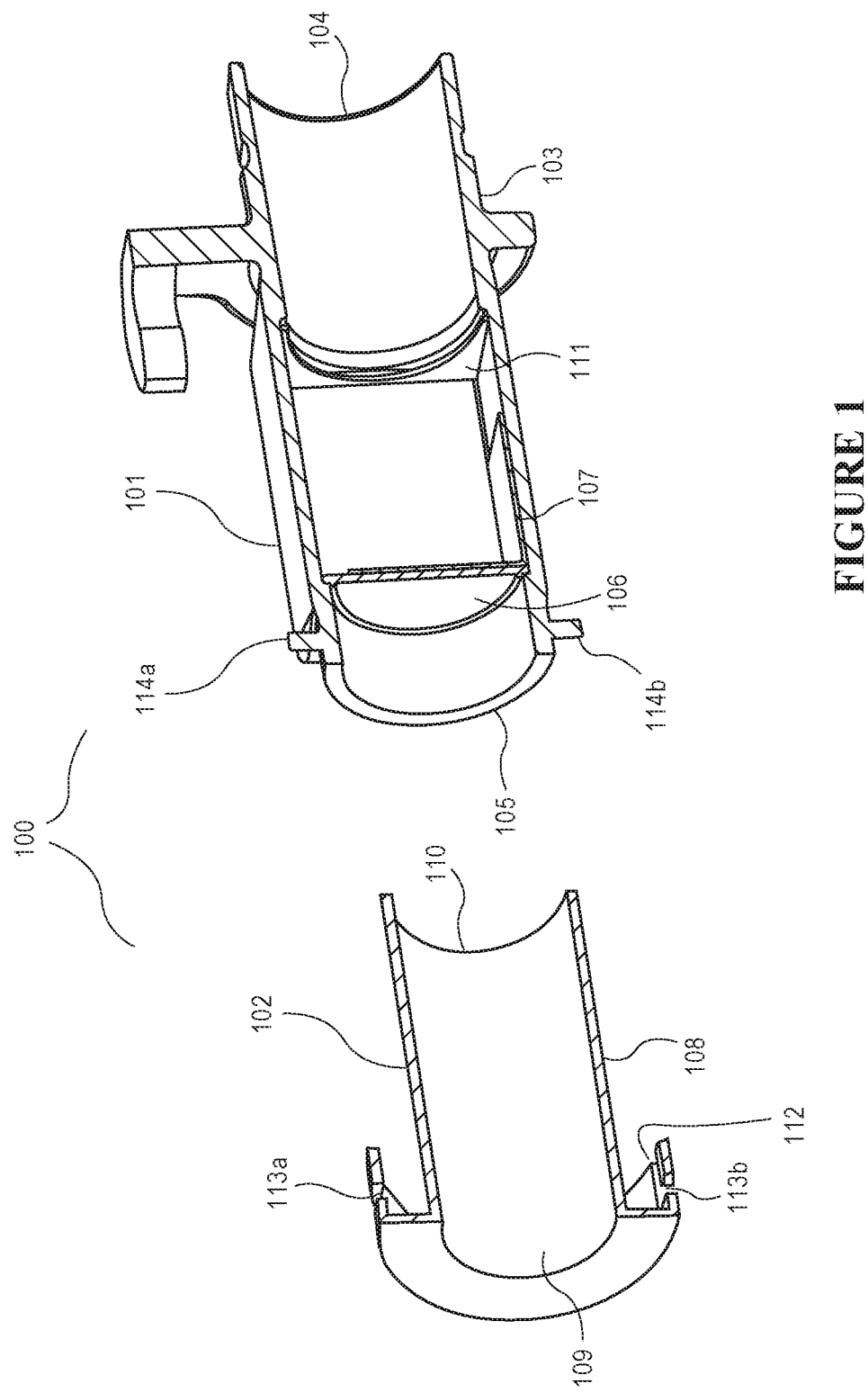
FIG. 1 illustrates a schematic cross-sectional view of a first embodiment of a bag connector system; in this particular figure, the coupling elements are aligned for coupling and the bag connector system is in the uncoupled state.
Figure 2A:
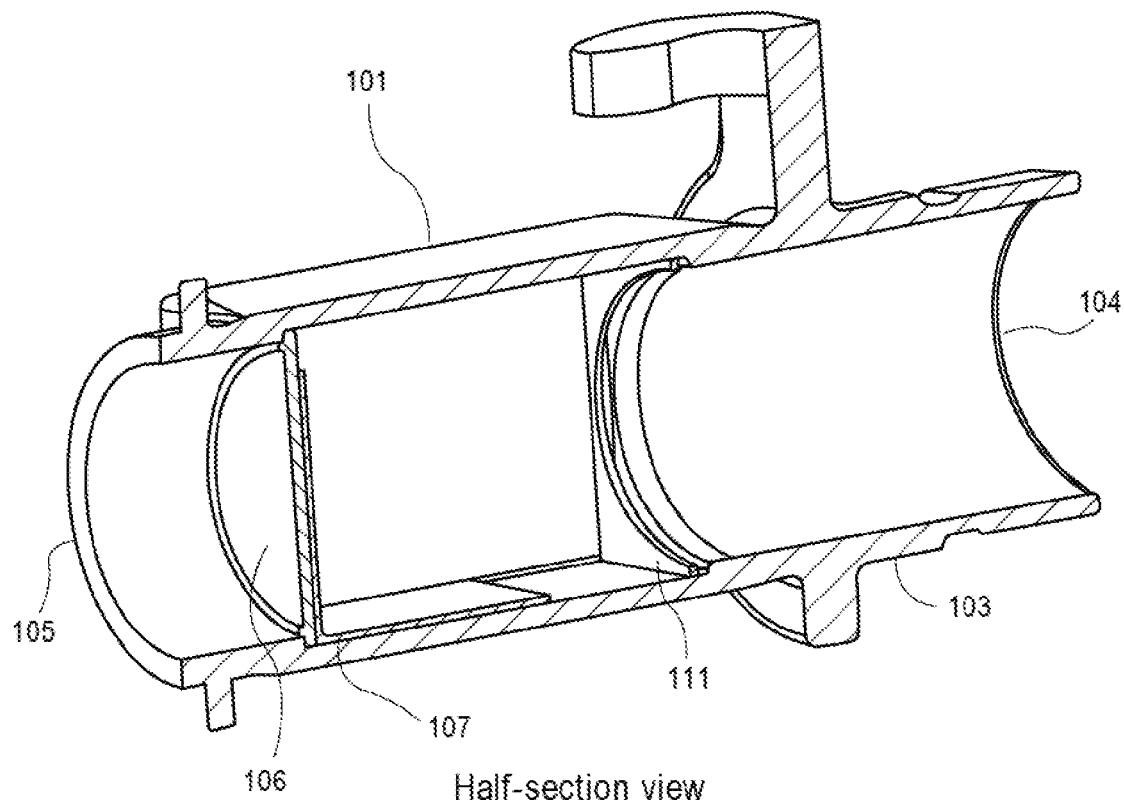
FIG. 2a illustrates a schematic cross-sectional view of the first coupling element of the bag connector system of FIG. 1.
Figure 2B:
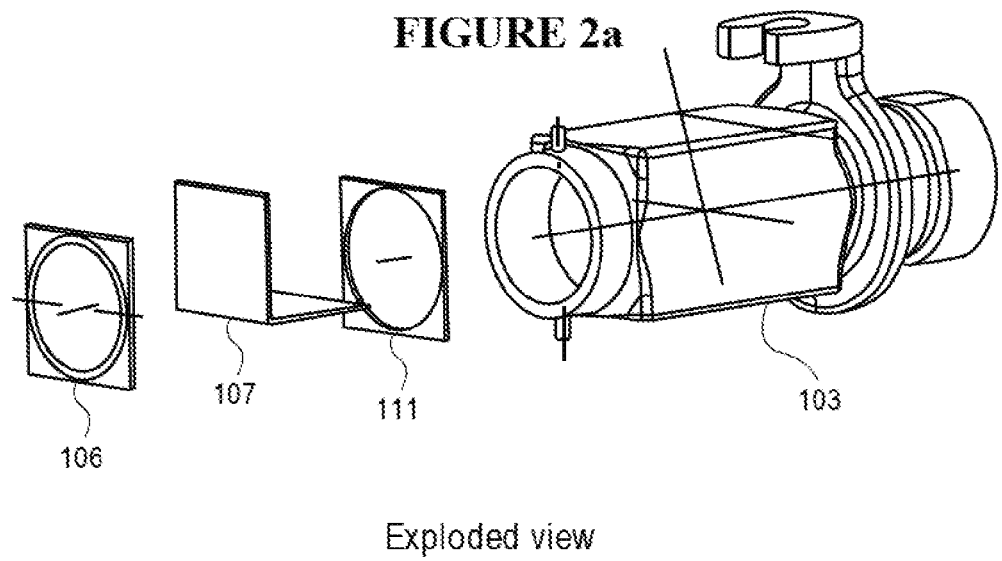
FIG. 2b illustrates an exploded view of the first coupling element of the bag connector system of FIG. 1.
Figure 2C:
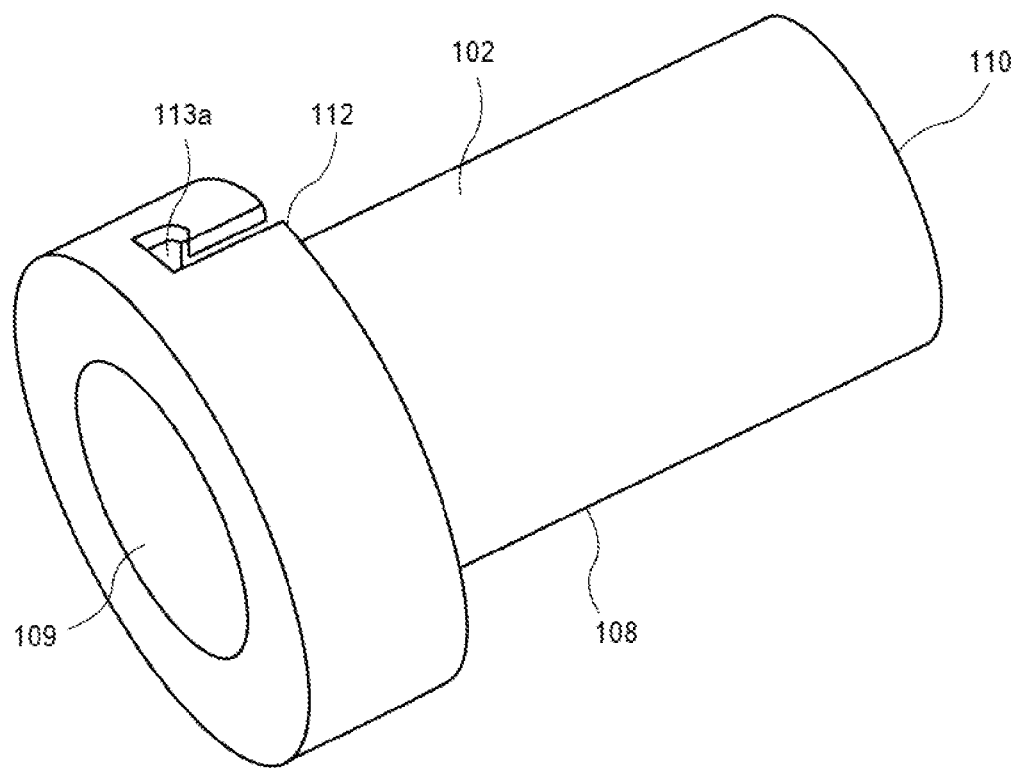
FIG. 2c illustrates a perspective view of the second coupling element of the bag connector system of FIG. 1.

Provided herein are bag connector systems to be used in a medical appliance. These bag connector systems provide a simple method to connect tubing that directs the flow of waste to an external waste collection bag while minimizing the exposure of the waste inside the tubing to the outside environment. When the two coupling elements of the bag connector system are coupled together, the drainage path between the tubing and the waste collection bag is activated to open. When the two coupling elements of the bag connector system are uncoupled or disconnected, the coupling element attached to the tubing will automatically close to contain the waste in the tubing and in the coupling element attached to the tubing. As such, the outer surfaces of the coupling element attached to the tubing will have minimum exposure of the contamination of the waste.

Medical Appliance with Bag Connector System

Disclosed herein, in certain embodiments, are medical appliances for the management of fecal or urinary waste. In some embodiments, the medical appliances comprise a catheter, an external waste storage container, and a bag connector system that connects the catheter to the external waste storage container. In further embodiments, the connection to the bag connector system is through the use of medical grade tubing. In other embodiments, the bag connector system is directly connected to the external waste storage container and/or to the catheter. In some embodiments, the medical grade tubing is draining tubing from the catheter. In some embodiments, the catheter is a rectal catheter. In other embodiments, the catheter is a urinary catheter.

In some embodiments, the medical appliances comprise a catheter, an external waste collection container, an external waste storage container, and a bag connector system that connects the waste collection container to the waste storage container. In further embodiments, the connection to the bag connector system is through the use of medical grade tubing. In other embodiments, the bag connector system is directly connected to the external waste collection container and/or external waste storage container. In some embodiments, the catheter is a rectal catheter. In other embodiments, the catheter is a urinary catheter.

In some embodiments, the bag connector system comprises a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element. In some embodiments, the self-closing seal is positioned within the housing of the first coupling element. In other embodiments, the self-closing seal is positioned outside of the housing of the first coupling element.

Disclosed herein, in certain embodiments, are medical appliances comprising a fluid storage container and a bag connector system, the bag connector system comprising a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element; and wherein the fluid outlet end of the second coupling element is connected to the fluid storage container and uncoupling of the first coupling element and the second coupling element results in minimal fluid contamination on the outer surfaces of the coupling elements. In some embodiments, the self-closing seal is positioned within the housing of the first coupling element. In other embodiments, the self-closing seal is positioned outside of the housing of the first coupling element.

In some embodiments, the self-closing seal is a duckbill valve, a flapper connected to a leaf spring, a sliding cover connected to a spring element, or a spring-loaded valve.

In some embodiments, each of the first coupling element and the second coupling element further comprises a means to maintain the first coupling element and the second coupling element in a coupled state. In further embodiments, the means to maintain the first coupling element and the second coupling element in a coupled state is selected from an interference fit mechanism, a twist lock-in (bayonet latch) mechanism, an annular snap-fit mechanism, a single cantilever snap-fit mechanism, and a multiple cantilever snap-fit mechanism comprising a plurality of cantilever snaps at the fluid outlet port of the first coupling element which forms a snap-fit with the sliding cover on the second coupling element. In still further embodiments, the means to maintain the first coupling element and the second coupling element in a coupled state is selected from a twist lock-in mechanism, a single cantilever snap-fit mechanism, and a multiple cantilever snap-fit mechanism comprising a plurality of cantilever snaps at the fluid outlet port of the first coupling element which forms a snap-fit with the sliding cover on the second coupling element.

In some embodiments, the medical grade tubing is made of silicone, PVC, rubber, polyurethane, or other suitable material. In various embodiments, the medical grade tubing can have an inner diameter of 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19, 20, 21, 22, 23, 24, 25 millimeters, or more, including increments therein.

Bag Connector System

Disclosed herein, in certain embodiments, are medical devices for the management of fecal or urinary waste. In some embodiments, a medical device disclosed herein comprises a bag connector system. In further embodiments, a bag connector system comprises a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element. In still further embodiments, the self-closing seal allows the uncoupling of the first coupling element and the second coupling element to result in minimal fluid contamination on the outer surfaces of the coupling elements. In some embodiments, the self-closing seal is positioned within the housing of the first coupling element. In other embodiments, the self-closing seal is positioned outside of the housing of the first coupling element.

In some embodiments, minimal fluid contamination on the outer surfaces of the coupling elements upon uncoupling of the first coupling element and second coupling element is little to no detectable fluid contamination on the outer surfaces of the coupling elements. In some embodiments, minimal fluid contamination on the outer surfaces of the coupling elements upon uncoupling of the first coupling element and second coupling element is negligible or limited fluid contamination on the outer surfaces of the coupling elements. In some embodiments, minimal fluid contamination on the outer surfaces of the coupling elements upon uncoupling of the first coupling element and second coupling element is little to no detectable fluid contamination to negligible or limited fluid contamination on the outer surfaces of the coupling elements.

In some embodiments, the housing of the coupling element is made of plastic or any other suitable material for containing and directing fluid, or a combination of such suitable materials.

In some embodiments, the self-closing seal is a check valve or a sliding cover connected to a spring element. In some embodiments, the self-closing seal is a duckbill valve, a flapper connected to a leaf-spring; a sliding cover connected to a spring element, or a spring-loaded valve. In some embodiments, the sliding cover and spring element are joined to form a unitary object. In other embodiments, the sliding cover and spring element are separate objects in direct contact with one another.

In some embodiments, the self-closing seal is a check valve. In some embodiments, the check valve is a ball check valve, a diaphragm check valve, a swing check valve, a stop-check valve, a lift-check valve, an in-line check valve or a duckbill valve. In some embodiments, the check valve is a ball check valve. In some embodiments, the check valve is a diaphragm check valve. In some embodiments, the check valve is a swing check valve. In some embodiments, the check valve is a stop-check valve. In some embodiments, the check valve is a lift-check valve. In some embodiments, the check valve is an in-line check valve. In some embodiments, the check valve is a leaf valve. In some embodiments, the check valve is a duckbill valve.

In some embodiments, the self-closing seal is a flapper connected to a leaf-spring; a sliding cover connected to a spring element, or a spring-loaded valve.

In some embodiments, the self-closing seal is a flapper connected to a leaf-spring. In some embodiments, the flapper is made of rubber or other elastomer. In some embodiments, the leaf-spring is made of metal, plastic, rubber, or other elastomer. In some embodiments, the flapper and the leaf-spring are an integrated piece or may comprise separately manufactured pieces joined together.

In some embodiments, the self-closing seal is a sliding cover connected to a spring element. In some embodiments, the sliding cover is made of plastic or other suitable material. In some embodiments, the spring element is made of metal, plastic, or rubber.

In some embodiments, the self-closing seal is a spring-loaded valve. In further embodiments, the spring-loaded valve comprises a spring seat, a spring element, and a flat cover. In still further embodiments, the spring-loaded valve is a poppet valve. In some embodiments the spring-loaded valve is an integrated piece or may comprise separately manufactured pieces joined together. In some embodiments, the spring seat is made of plastic or metal. In some embodiments, the spring element is made of plastic or metal. In some embodiments, the flat cover is made of silicone, rubber, or other elastomer.

In some embodiments, each of the first coupling element and the second coupling element further comprises a means to maintain the first coupling element and the second coupling element in a coupled state. In some embodiments, the means to maintain the first coupling element and the second coupling element in a coupled state is a locking mechanism. In some embodiments, the locking mechanism is selected from a twist lock-in (bayonet latch) mechanism, a single cantilever snap-fit mechanism, a multiple cantilever snap-fit mechanism, an annular snap-fit mechanism, or an interference fit mechanism. In some embodiments, the locking mechanism is a twist lock-in mechanism. In some embodiments, the locking mechanism is a single cantilever snap-fit mechanism. In some embodiments, the locking mechanism comprises a plurality of cantilever snaps at the fluid outlet port of the first coupling element which forms a snap-fit with the sliding cover on the second coupling element. In some embodiments, the first coupling element and the second coupling element further comprises complementary components of a locking mechanism. In further embodiments, components of a locking mechanism are part of the fluid outlet port of the first coupling element and part of the fluid inlet end of the second coupling element. In some embodiments, the first coupling element further comprises a washer. In some embodiments, the washer is made of silicone, fiber, rubber, or other elastomer. In some embodiments, the washer is a flat ring with a polyhedral or circular shape and a circular central opening. In some embodiments, the washer is a tapered ring.

In some embodiments the second coupling element further comprises at least one O-ring. In some embodiments, the second coupling element further comprises an O-ring positioned on the outer surface of the housing. In some embodiments, the O-ring is made of silicone, rubber, or other elastomer.

In some embodiments, the second coupling element further comprises a sliding cover positioned over the fluid inlet port. In some embodiments, the sliding cover is made of plastic or other suitable material, or combination of such materials. In some embodiments, the sliding cover is self-closing and is connected to a spring element.

In some embodiments, the second coupling element further comprises a check valve. In some embodiments, the check valve is a ball check valve, a diaphragm check valve, a swing check valve, a stop-check valve, a lift-check valve, an in-line check valve or a duckbill valve. In some embodiments, the check valve is a ball check valve. In some embodiments, the check valve is a diaphragm check valve. In some embodiments, the check valve is a swing check valve. In some embodiments, the check valve is a stop-check valve. In some embodiments, the check valve is a lift-check valve. In some embodiments, the check valve is an in-line check valve. In some embodiments, the check valve is a leaf valve. In some embodiments, the check valve is a duckbill valve.

Referring to FIGS. 1, 2a-c, and 3a-b, a first embodiment of a bag connector system 100 comprises a first coupling element 101 and a second coupling element 102. The first coupling element 101 comprises a housing 103 having a fluid inlet port 104 and a fluid outlet port 105. The second coupling element 102 comprises a housing 108 having a fluid outlet end 109 and a fluid inlet end 110. Housing 103 and housing 108 may be made of plastic or any material suitable for containing and directing fluid.

The first coupling element 101 also comprises a flapper 106 attached to a leaf spring 107. The flapper 106 may be made of resilient material such as rubber or other elastomer. The leaf spring 107 may be made of metal, plastic, rubber or other elastomer. The flapper 106 and the leaf spring 107 can be an integrated piece made of metal, plastic, elastomer and other suitable material, or may comprise two separately manufactured pieces joined together.

Referring to FIG. 1, in the uncoupled state of the bag connector system 100, the flapper 106 automatically provides a seal within the housing 103 that prevents the exit of fluid from the housing 103 through the fluid outlet port 105. The leaf spring 107 provides slight compression to the flapper 106 to automatically place the flapper 106 in this sealed position when in its uncoupled state, and to maintain this sealed position.

Figure 3A:
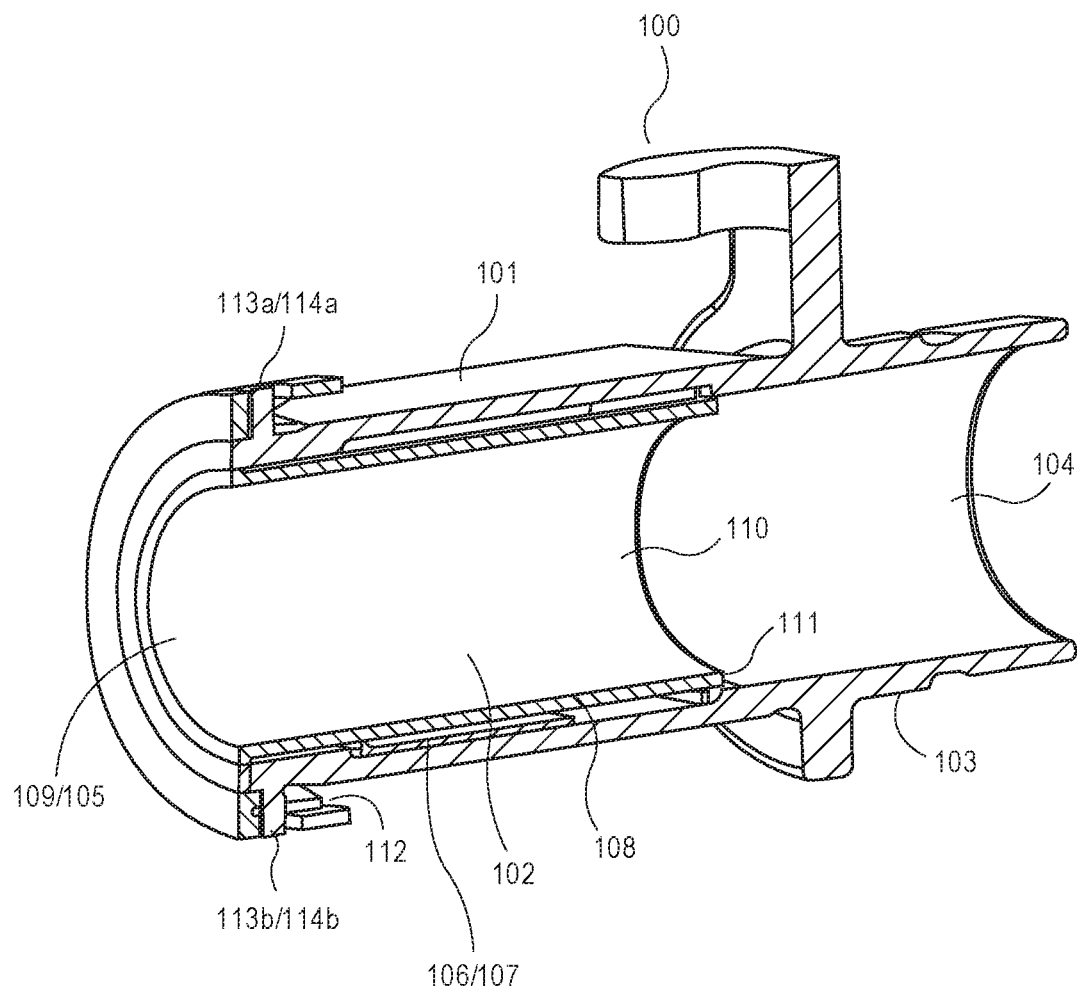
FIG. 3a illustrates a schematic cross-sectional view of the bag connector system of FIG. 1; in this particular figure, the coupling elements are coupled, the washer is a flat ring, and the bag connector system is in the coupled state.

Referring to FIG. 3a, in the coupled state of the bag connector system 100, the flapper 106 is obstructed by the second coupling element 102. The fluid inlet end 110 of the second coupling element 102 pushes against the flapper 106, partially or completely obstructing the flapper 106 and eliminating the seal which was created and maintained by the flapper and leaf-spring mechanisms during the uncoupled state. In this way, fluid within the housing 103 can flow through the coupled bag connector system 100 and be collected in a fluid storage container connected to the fluid outlet end 109 of the second coupling element 102.

Figure 3B:
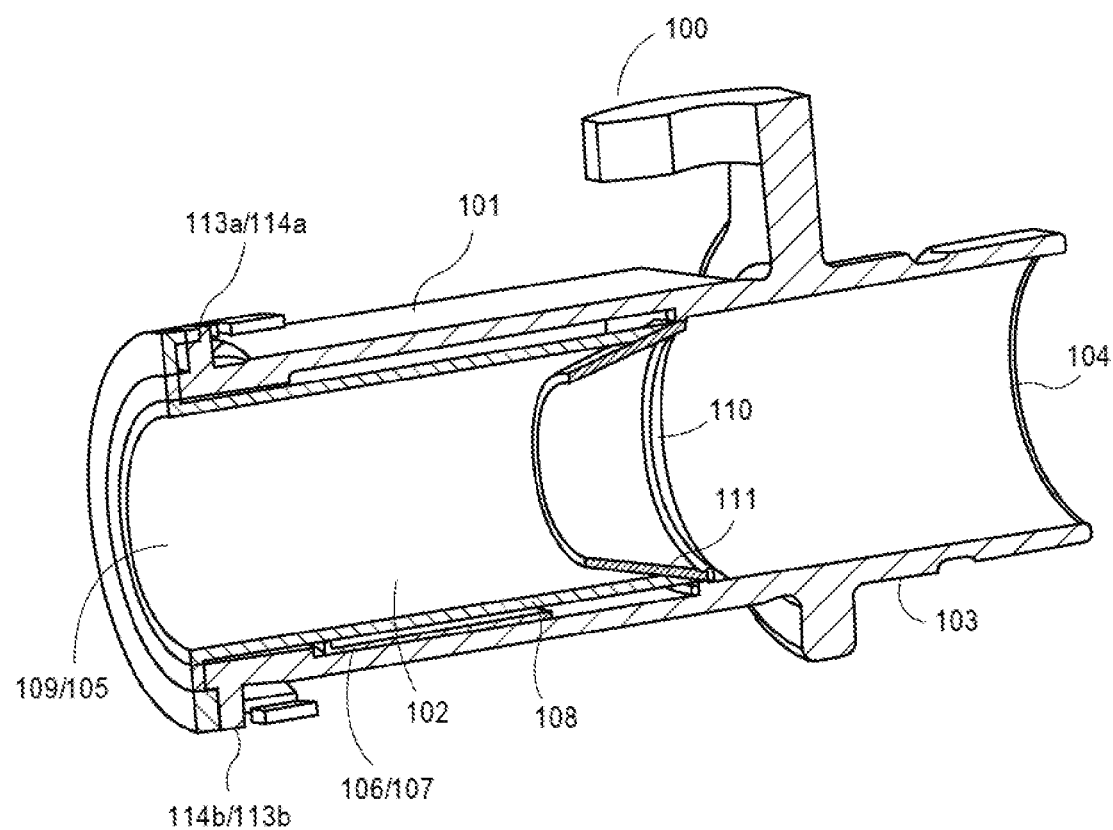
FIG. 3b illustrates a schematic cross-sectional view of an alternative embodiment of the bag connector system of FIG. 3a; in this particular figure, the washer is a tapered ring.

The first coupling element 101 may further comprise a washer 111 that interacts with the second coupling element 102 during the coupled state to create and maintain a seal between the second coupling element 102 and the first coupling element 101. Referring to FIGS. 3a and 3b, the fluid inlet end 110 of the second coupling element 102 comes in contact with the washer 111 to create this seal. The washer 111 may be made of silicone, rubber, or another elastomer. In terms of shape, the washer may be a ring (FIG. 3a) or a tapered ring (FIG. 3b).

Each of the first coupling element 101 and the second coupling element 102 further comprises complementary components of a locking mechanism, which maintains the first coupling element and the second coupling element in a coupled state. Such locking mechanisms include a twist lock-in mechanism, bayonet latch, or other locking mechanism which maintains a coupled state between the first coupling element and the second coupling element. For example, in one embodiment the external edge of the fluid outlet end 109 of the second coupling element 102 is a rotatable locking member 112 having two slots 113a and 113b which receive pins 114a and 114b located on the outer surface of the fluid outlet port 105. When the twist lock-in mechanism is in a first position, the pins 114a and 114b can pass through the complementary slots 113a and 113b, easily coupling or uncoupling the first coupling element 101 and the second coupling element 102. When the twist lock-in mechanism is in a second position, the pins 114a and 114b cannot pass through the complementary slots 113a and 113b, maintaining the first coupling element 101 and the second coupling element 102 in a coupled state. The twist lock-in mechanism is toggled between the first and second positions by rotating the coupled coupling elements in opposing directions along the axis of the fluid flow pathway.

Referring to FIGS. 4, 5a-c, 6, and 7, a second embodiment of a bag connector system 200 comprises a first coupling element 201 and a second coupling element 202. The first coupling element 201 comprises a housing 203 having a fluid inlet port 204 and a fluid outlet port 205. The second coupling element 202 comprises a housing 208 having a fluid outlet end 209 and a fluid inlet end 210. Housing 203 and housing 208 may be made of plastic or any material suitable for containing and directing fluid.

The first coupling element 201 also comprises a sliding cover 206 attached to a spring element 207. Like housing 203, the sliding cover 206 may be made of plastic or any suitable material. The spring element 207 may be made of metal, plastic, or rubber.

Figure 4:
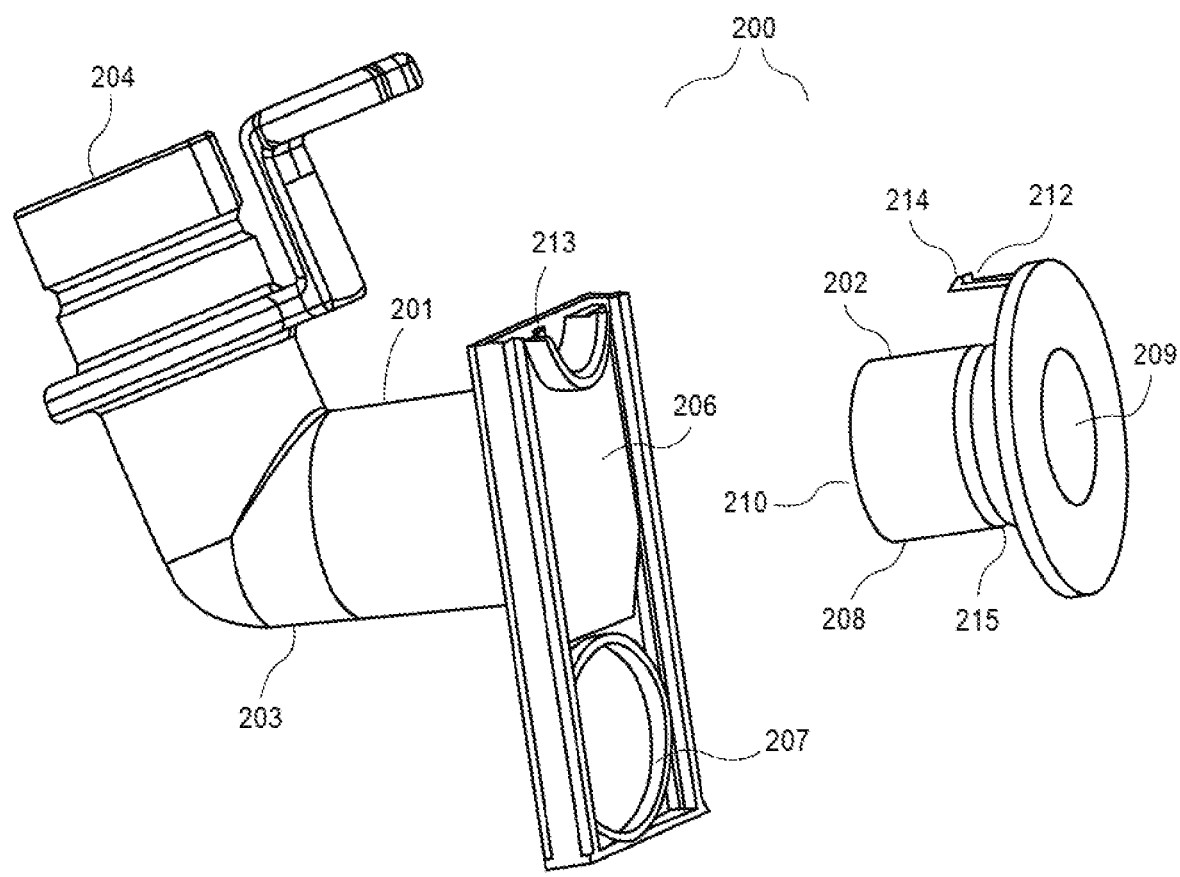
FIG. 4 illustrates a perspective view of a second embodiment of a bag connector system; in this particular figure, the coupling elements are aligned for coupling and the bag connector system is in the in the uncoupled state
Figure 5A:
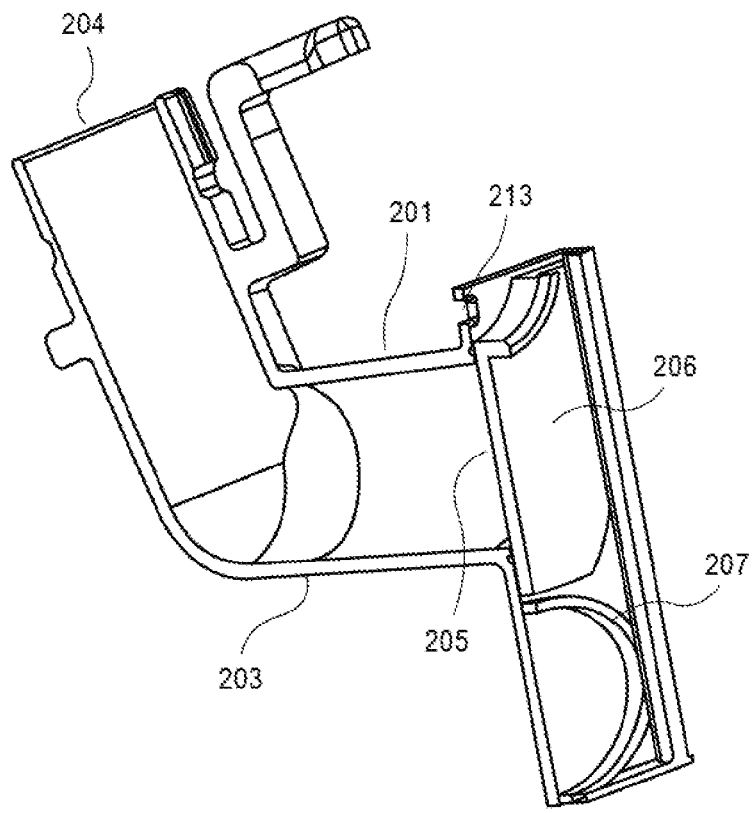
FIG. 5a illustrates a schematic cross-sectional view of the first coupling element of the bag connector system of FIG. 4.
Figure 5B:
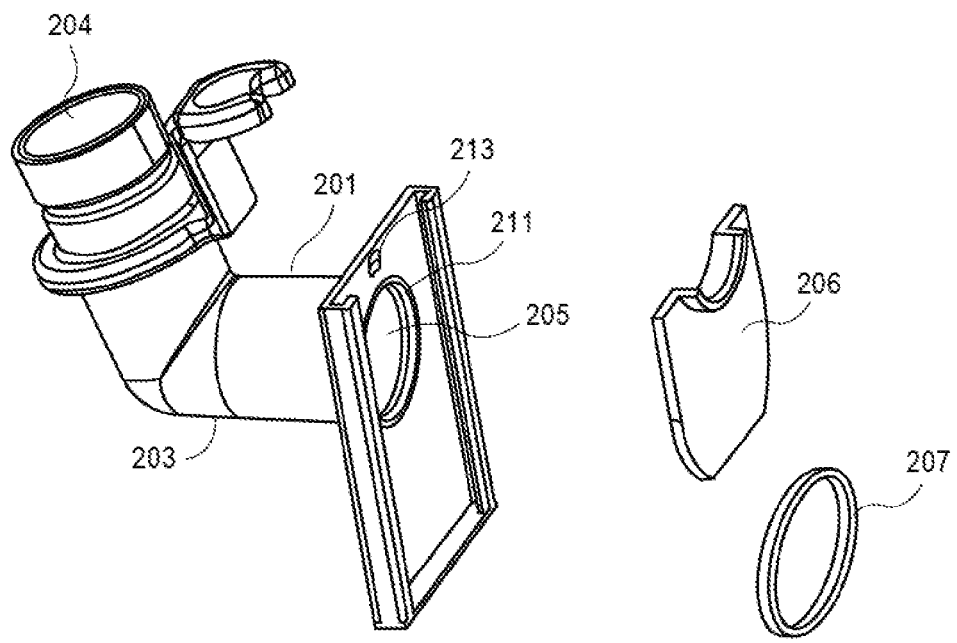
FIG. 5b illustrates an exploded view of the first coupling element of the bag connector system of FIG. 4.
Figure 5C:
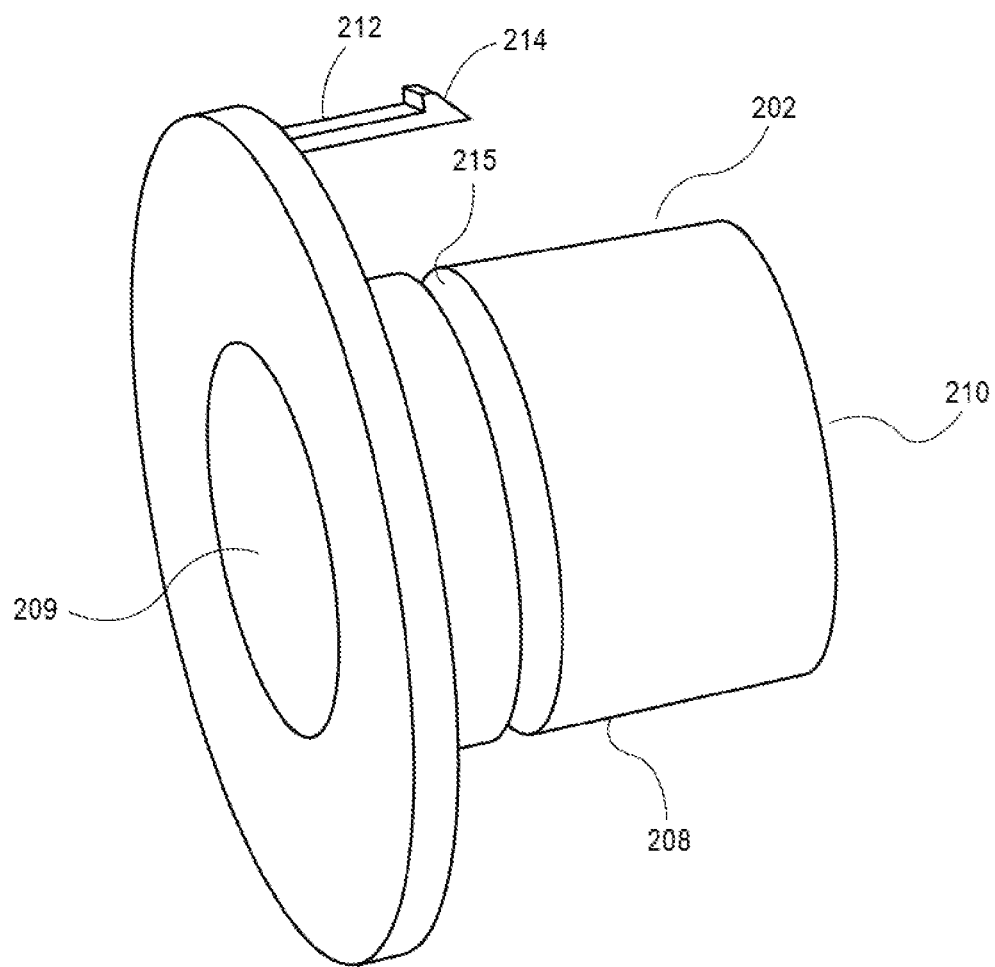
FIG. 5c illustrates a perspective view of the second coupling element of the bag connector system of FIG. 4

Referring to FIG. 4, in the uncoupled state of the bag connector system 200, the sliding cover 206 completely covers the fluid outlet port 205, preventing the exit of fluid from the housing 203 through the fluid outlet port 205. The spring element 207 provides slight compression to the sliding cover 206 to automatically place the sliding cover 206 over fluid outlet port 205 and maintain this sealed position in its uncoupled state.

Figure 6:
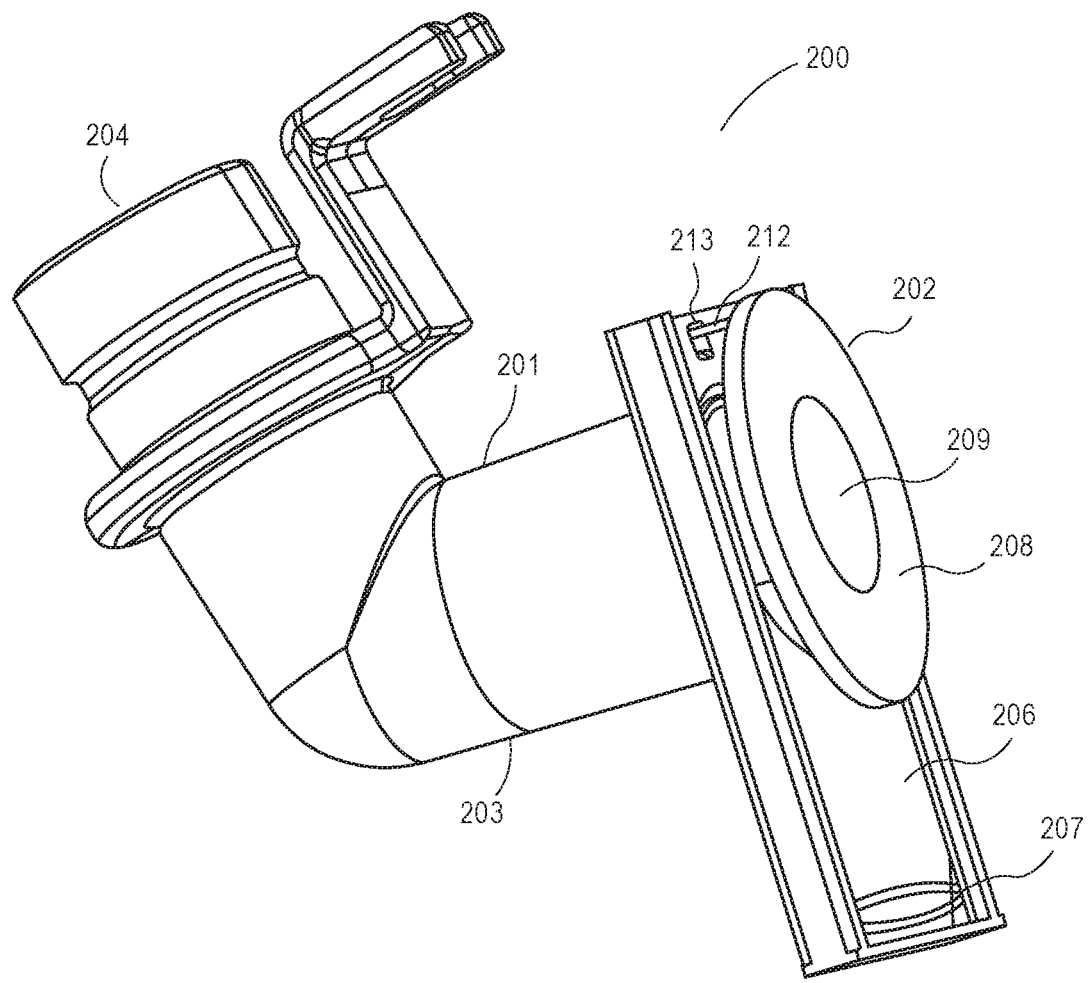
FIG. 6 illustrates a perspective view of the bag connector system of FIG. 4; in this particular figure, the coupling elements are coupled and the bag connector system is in the coupled state.
Figure 7:
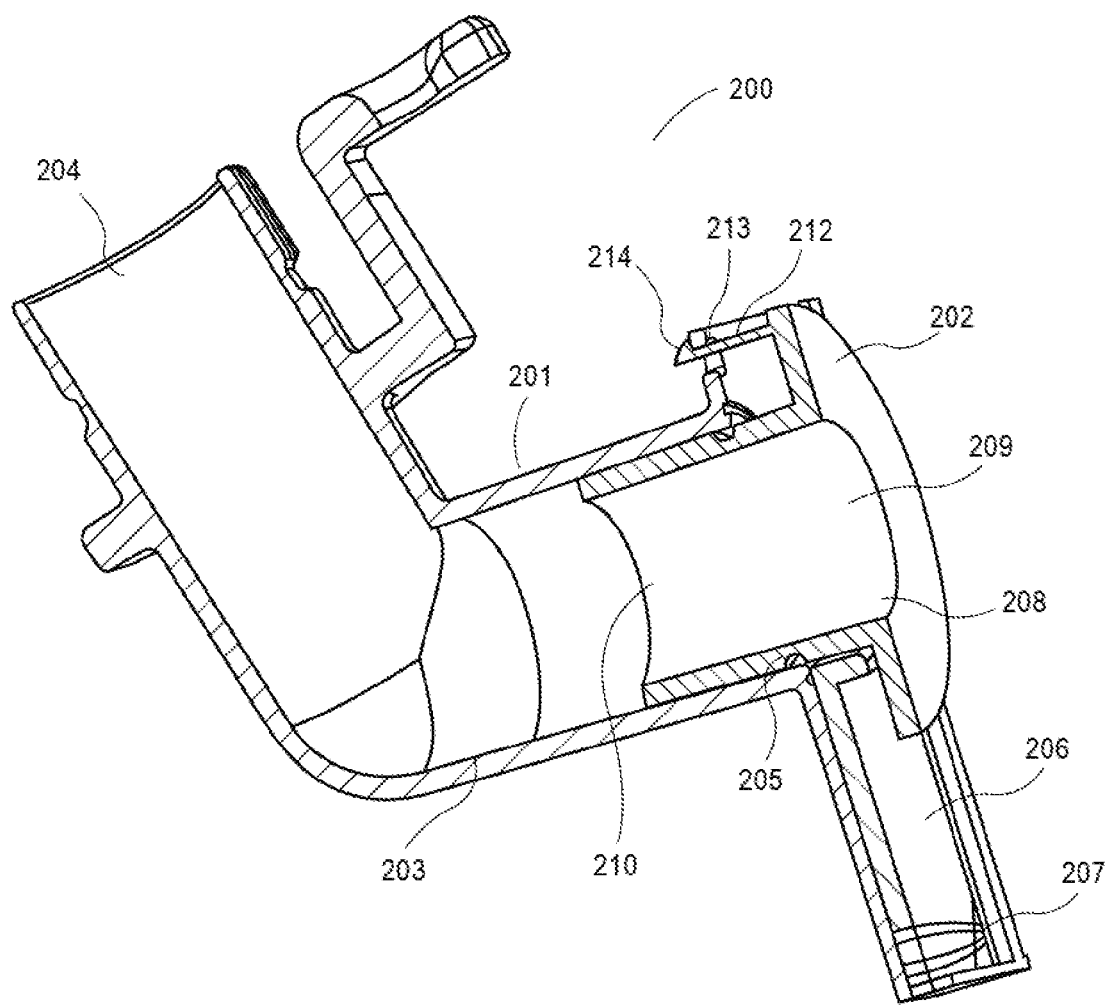
FIG. 7 illustrates a schematic cross-sectional view of the bag connector system of FIG. 4; in this particular figure, the coupling elements are coupled and the bag connector system is in the coupled state.
Figure 8:
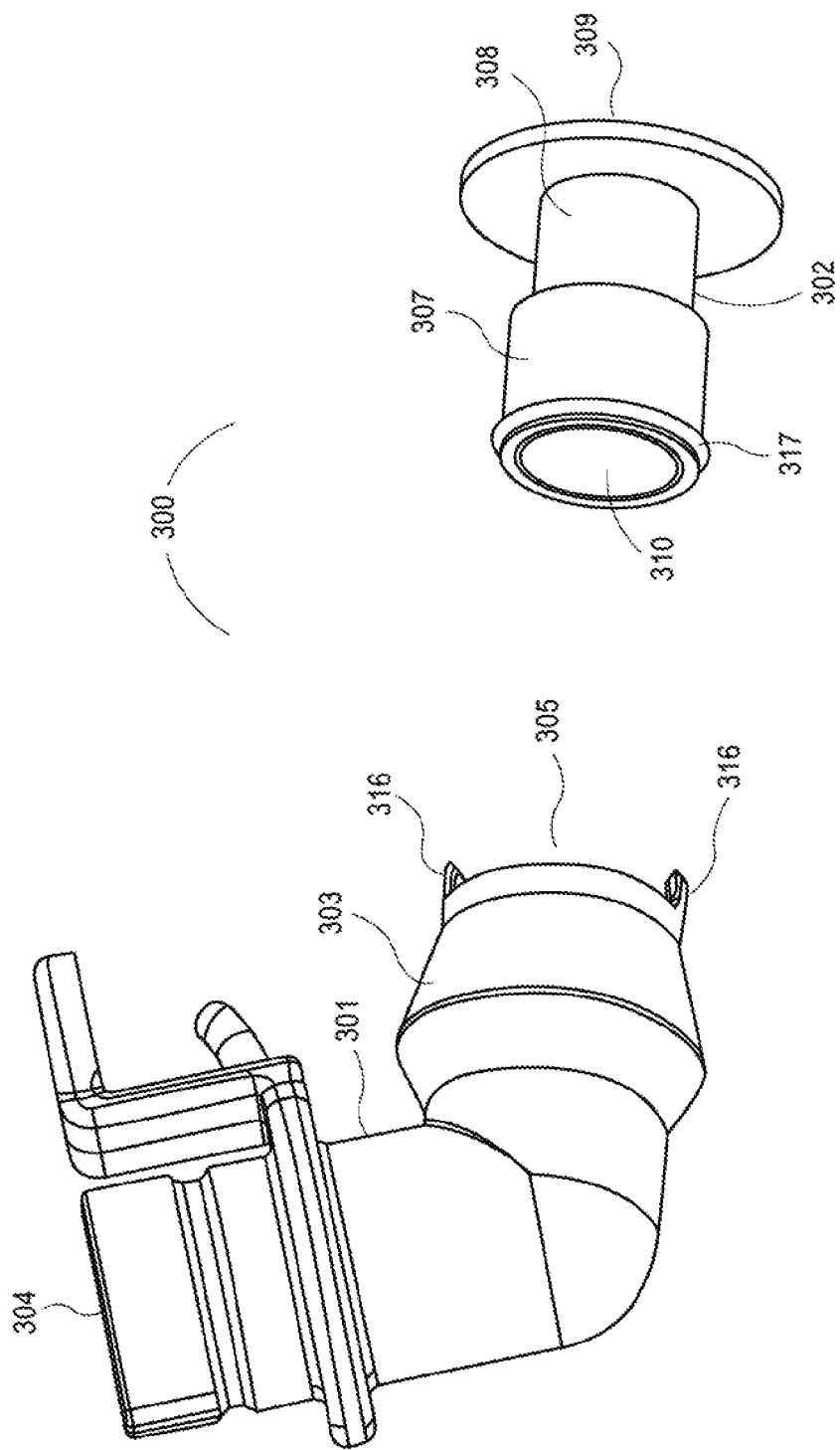
FIG. 8 illustrates a perspective view of a third embodiment of a bag connector system; in this particular figure, the coupling elements are aligned for coupling and the bag connector system is in the uncoupled state.
Figure 9A:
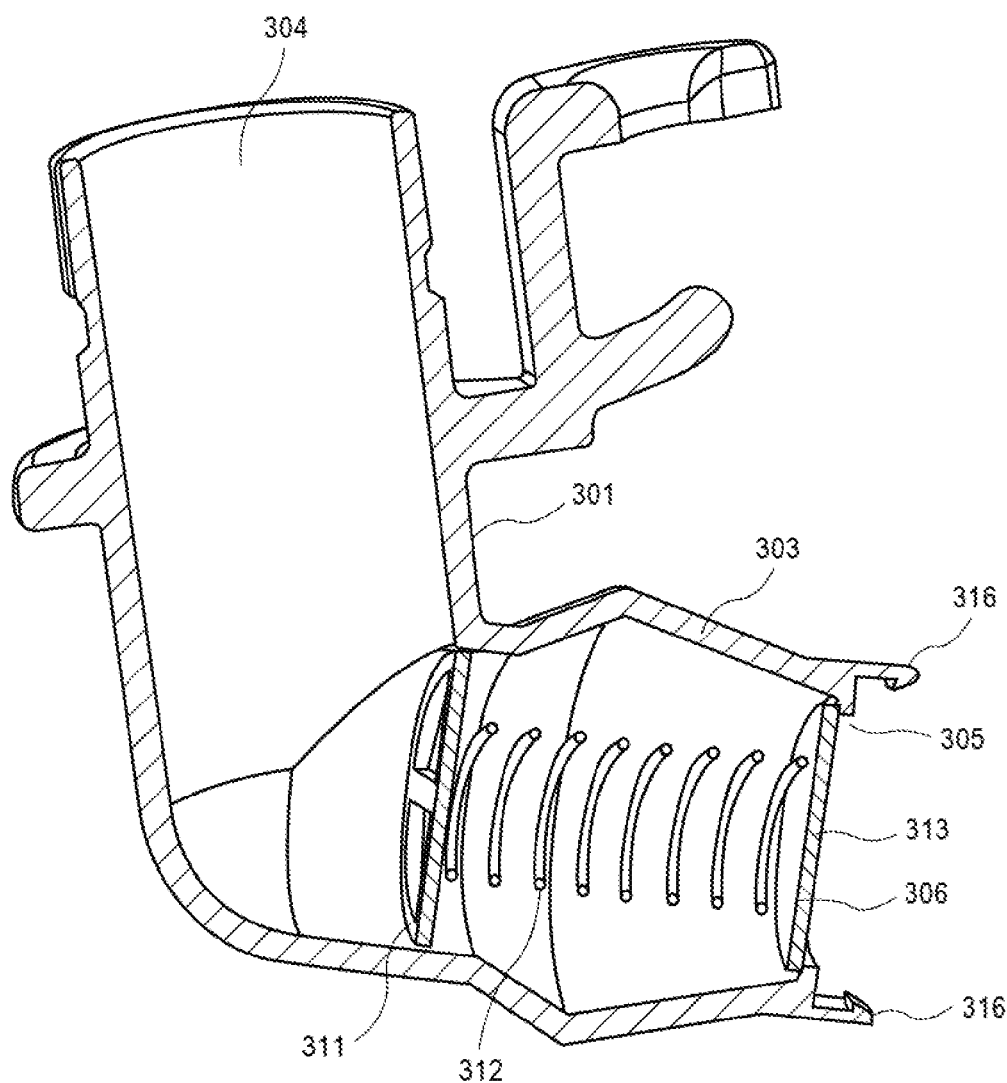
FIG. 9a illustrates a schematic cross-sectional view of the first coupling element the bag connector system of FIG. 8.
Figure 9B:
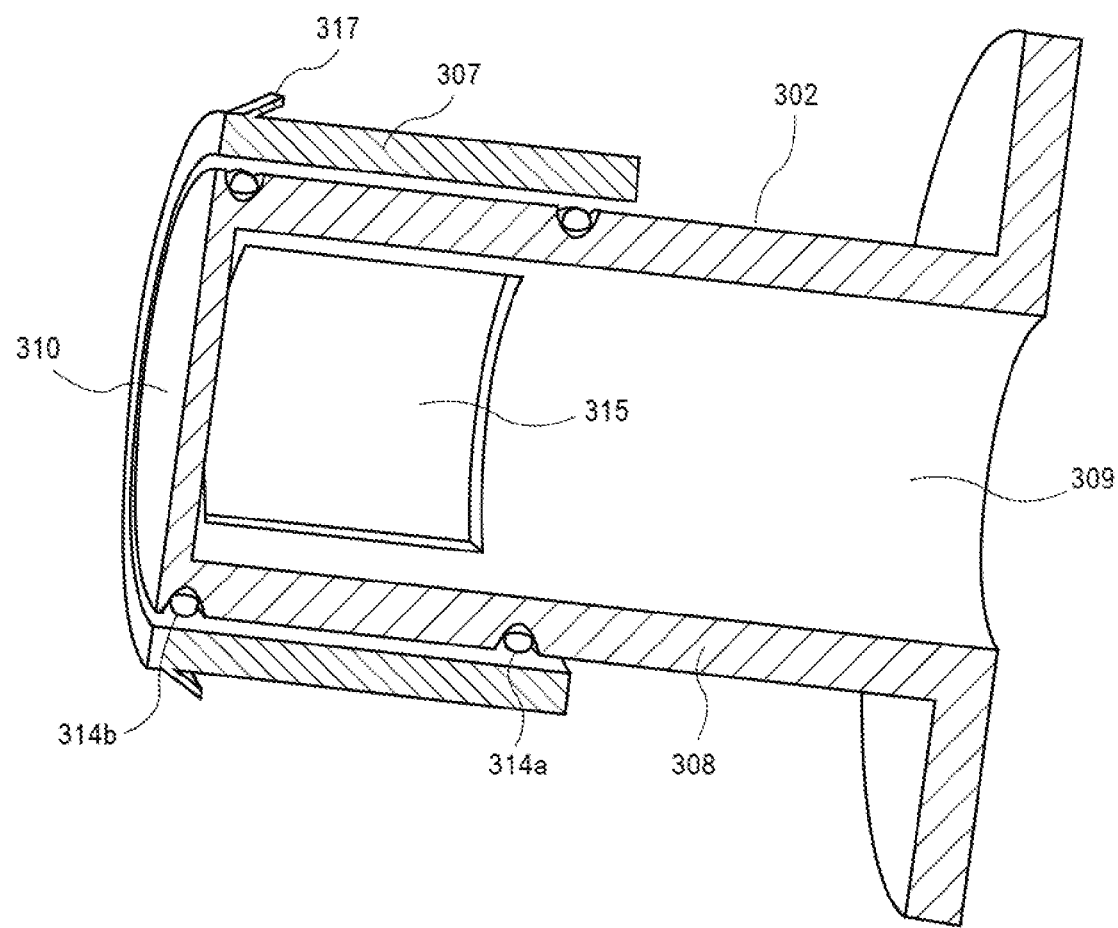
FIG. 9b illustrates a schematic cross-sectional view of the second coupling element of the bag connector system of FIG. 8.

Referring to FIG. 6, in the coupled state of the bag connector system 200, the sliding cover 206 is pushed towards the spring element 207 to expose the fluid outlet port 205 for coupling with the second coupling element 202. In this way, fluid within the housing 203 can flow through the coupled bag connector system 200 and be collected in a fluid storage container connected to the fluid outlet end 209 of the second coupling element 202.

The first coupling element 201 further comprises a washer 211, positioned just outside of the fluid outlet port 205, which interacts with the sliding cover 206 to create and maintain a seal with the sliding cover 206. The washer 211 may be made of silicone, fiber, rubber, or other elastomer.

The second coupling element 202 further comprises an O-ring 215, positioned around the outer surface of housing 208, which interacts with the inner surface of housing 203 at the fluid outlet port 205 to create and maintain a seal. The O-ring 215 may be made of silicone, rubber or other elastomer.

Each of the first coupling element 201 and the second coupling element 202 further comprises complementary components of a cantilever snap-fit mechanism, which can maintain the first coupling element and the second coupling element in a coupled state. In the coupled state of the bag connector system 200, a cantilever snap 212 located on the second coupling element 202 fits into a complementary slot 213 located on the sliding cover 206. The hook 214 prevents the cantilever snap 212 from being removed from slot 213, maintaining the coupling state of the first coupling element 201 and the second coupling element 202. One method to uncouple bag system 200 is to simultaneously depress hook 214 in a radial direction towards housing 203 and pull the coupling elements 201 and 202 apart.

Referring to FIGS. 8, 9a-b, 10, and 11, a third embodiment of a bag connector system 300 comprises a first coupling element 301 and a second coupling element 302. The first coupling element 301 comprises a housing 303 having a fluid inlet port 304 and a fluid outlet port 305. The second coupling element 302 comprises a housing 308 having a fluid outlet end 309 and a fluid inlet end 310. The fluid inlet end 310 has at least two openings 315 to allow fluid flow into the housing 308. A plurality of cantilever snaps 316 is located at the outer edge of fluid outlet port 305 and serves as a component of a snap-fit mechanism. Housing 303 and housing 308 may be made of plastic or any material suitable for containing and directing fluid.

The first coupling element 301 also comprises a spring loaded valve 306. The spring loaded valve 306 comprises of a spring seat 311, a spring element 312, and a flat cover 313. The spring seat 311, the spring element 312, and the flat cover 313 may all be integrated as one piece or manufactured separately and joined together to form the spring loaded valve 306. The spring seat 311 is perforated in a suitable manner so as to allow fluid flow through the spring seat 311. The spring seat 311 may be made of plastic or metal. The spring element 312 may be made of metal or plastic. The flat cover may be made of silicone, rubber, or other elastomer.

The second coupling element 302 also comprises a sliding cover 307 in the form of a movable hollow cylindrical member made of plastic that surrounds the fluid inlet end 310 of the housing 308. A ridge 317 is located on the outer surface of the sliding cover 307 and serves as a component of a snap-fit mechanism.

Figure 10:
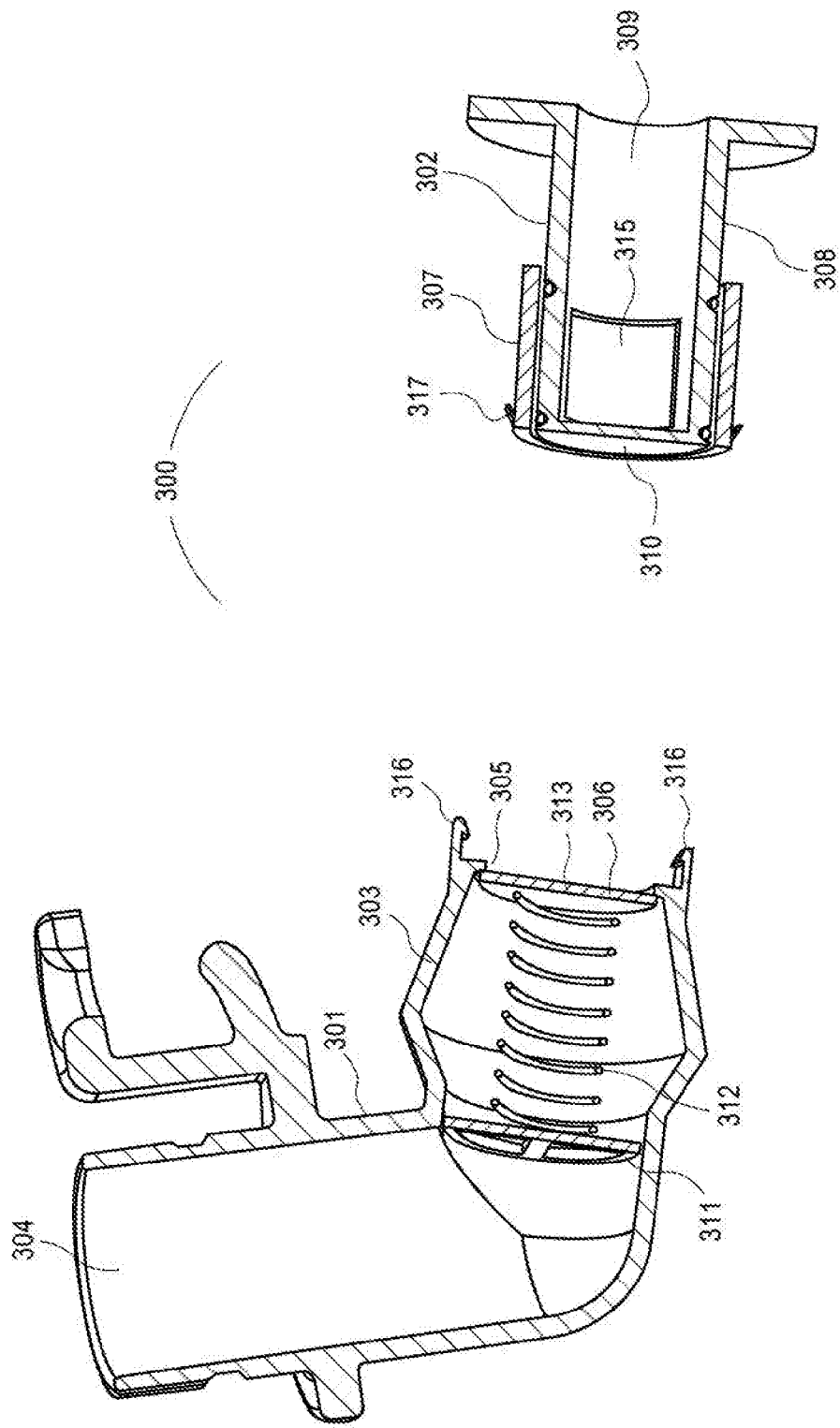
FIG. 10 illustrates a schematic cross-sectional view of the bag connector system of FIG. 8; in this particular figure, the coupling elements are aligned for coupling and the bag connector system is in the uncoupled state.

Referring to FIG. 10, in the uncoupled state of the bag connector system 300, the flat cover 313 of the spring loaded valve 306 is compressed against the inner wall of the fluid outlet port 305. The spring element 312 provides a slight compression, which creates and maintains a seal that prevents the exit of fluid through fluid outlet port 305. The sliding cover 307 surrounds the fluid inlet end 310 and completely covers the openings 315, creating a seal by interacting with O-rings 314a and 314b located on the outer surface of the fluid inlet port 310, at the distal and proximal ends of the openings 315. The O-rings 314a and 314b may be made of silicone, rubber, or other elastomer.

Figure 11:
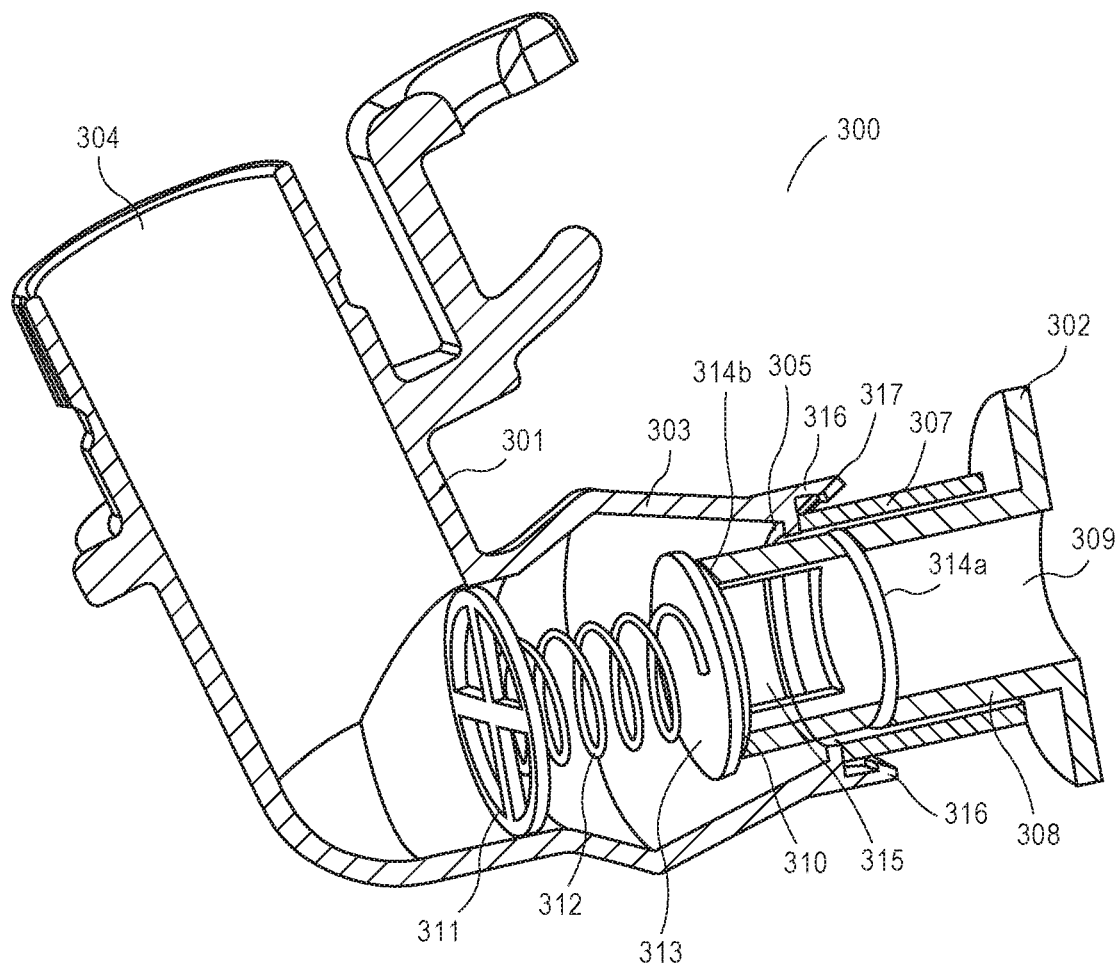
FIG. 11 illustrates a schematic cross-sectional view of the bag connector system of FIG. 8; in this particular figure, the coupling elements are coupled and the bag connector system is in the coupled state.

Referring to FIG. 11, in the coupled state of bag connector system 300, the flat cover 313 of the spring loaded valve 306 is pushed into the housing 303 by the fluid inlet end 310. Concomitantly, the sliding cover 307 is pushed by the outer edge of fluid outlet port 305 towards the fluid outlet end 309, providing complete or partial exposure of the openings 315 at the fluid inlet end 310. Fluid within the housing 303 can flow directly into fluid inlet end 310 through openings 315, as fluid inlet end 310 is positioned inside the housing 303. The plurality of cantilever snaps 316 on fluid outlet port 305 forms a snap-fit with the ridge 317 on the sliding cover 307. This snap-fit maintains the coupled state of the bag connector system 300

To uncouple the first coupling element 301 and the second coupling element 302, sufficient pressure is applied by pulling the coupling elements 301 and 302 in opposing directions away from the snap-fit to cause one or more cantilever snaps 316 to lift away from the ridge 317, weakening the snap-fit until the snap-fit is released. Prior to the release of the snap-fit, the pulling motion moves the fluid inlet end 310 out of the housing 303, freeing the spring loaded valve 306 to seal the housing 303, and moves the sliding cover 307 to once again fully cover the openings 315 of the fluid inlet end 310.

Referring to FIGS. 12-15, a fourth embodiment of a bag connector system 400 comprises a first coupling element 401 and a second coupling element 402. The first coupling element 401 comprises a housing 403 having a fluid inlet port 404 and a fluid outlet port 405. The fluid outlet port 405 comprises a cap 406 and at least one opening 407 to allow fluid flow out of the housing 403. The second coupling element 402 comprises a housing 408 having a fluid inlet end 409 and a fluid outlet end 410. Housing 403 and housing 408 may be made of plastic or any material suitable for containing and directing fluid.

The first coupling element 401 also comprises a spring element 411 connected to a sliding cover 412 in the form of a movable hollow cylindrical member made of plastic or any other suitable material and comprises at least two external flanges 413a and 413b. In a modified embodiment (not shown), the sliding cover 412 has only one external flange 413. The spring element 411 and the sliding cover 412 can be joined to form a unitary object or two separate objects in direct contact with one another.

The second coupling element 402 also comprises a duckbill valve 414 and a valve holder 415. The duckbill valve 414 is made of silicone, rubber, or other elastomer. The valve holder 415 is made of plastic or any other suitable material. The duckbill valve 414 and the valve holder 415 can be an integrated piece or may comprise two separately manufactured pieces joined together. In other contemplated embodiments (not shown), the second coupling element 402 comprises a valve holder and a check valve selected from a ball check valve, a diaphragm check valve, a swing check valve, a stop-check valve, a lift-check valve, and an in-line check valve.

Figure 12:
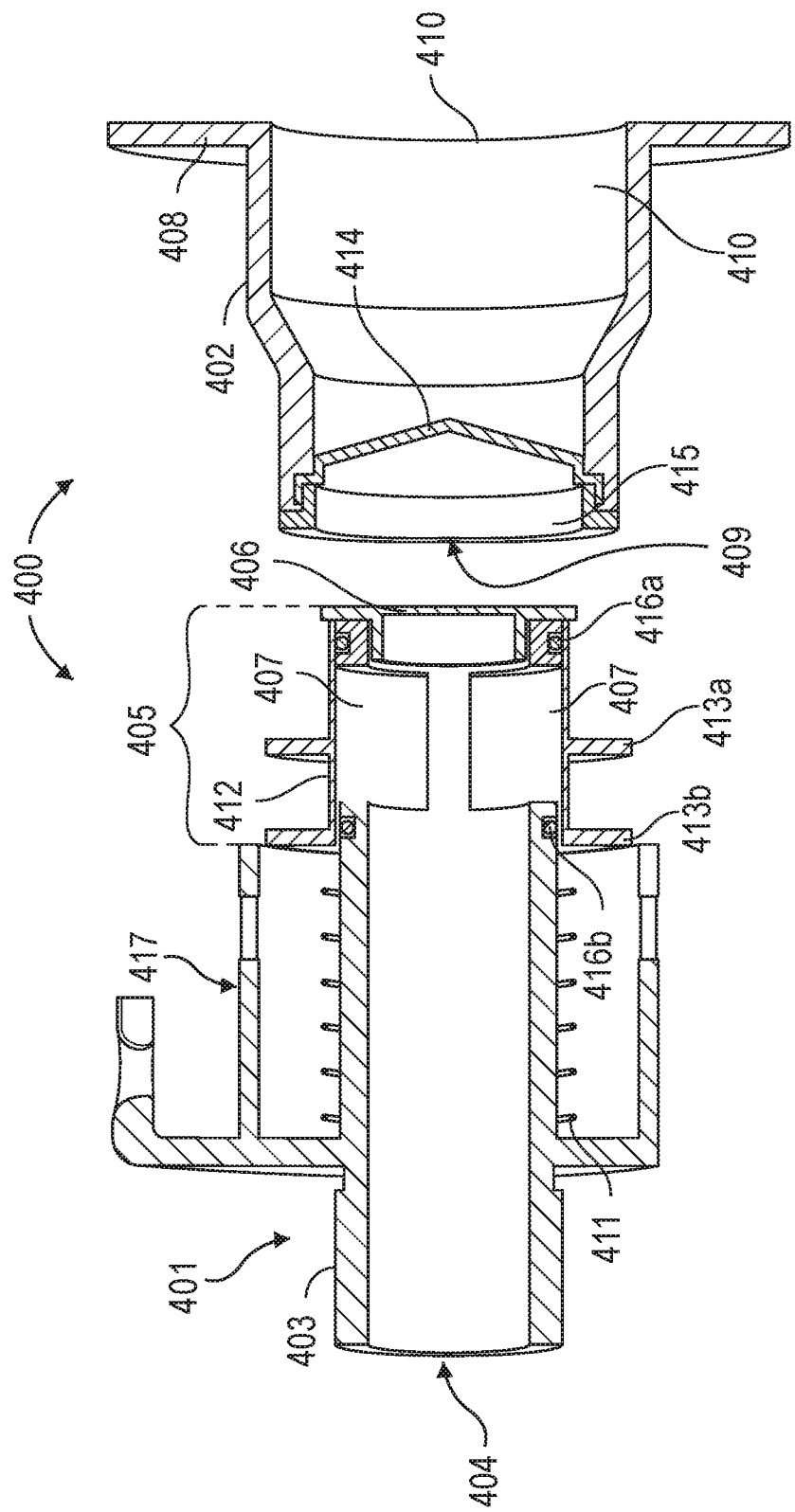
FIG. 12 illustrates a schematic cross-sectional view of a fourth embodiment of a bag connector system; in this particular figure, the coupling elements are aligned for coupling and the bag connector system is in the uncoupled state.
Figure 13:
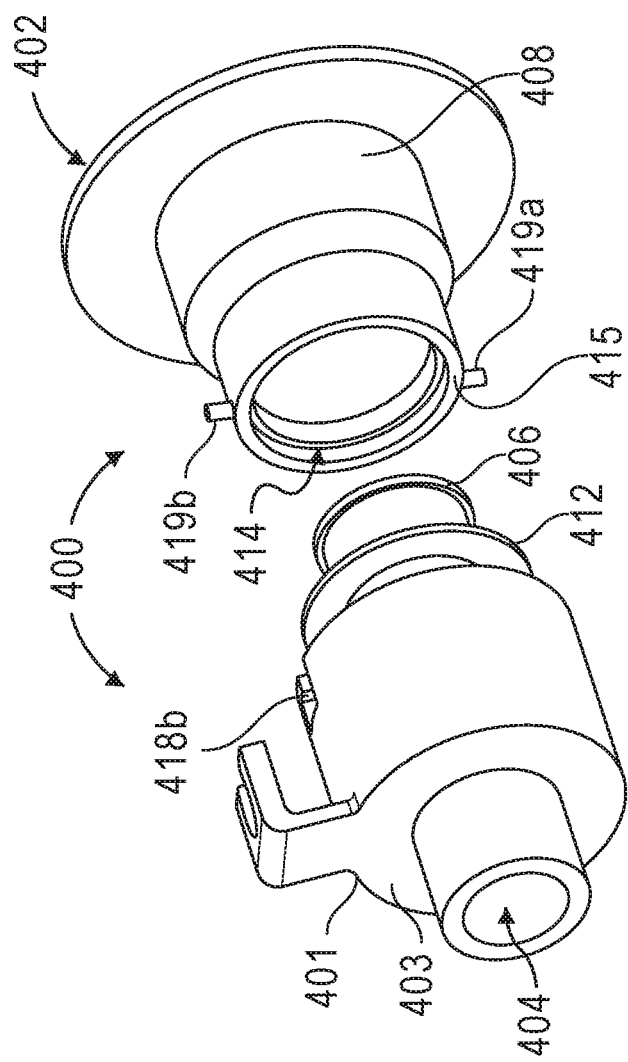
FIG. 13 illustrates a perspective view of the bag connector system of FIG. 12; in this particular figure, the coupling elements are aligned for coupling and the bag connector system is in the uncoupled state.
Figure 14:
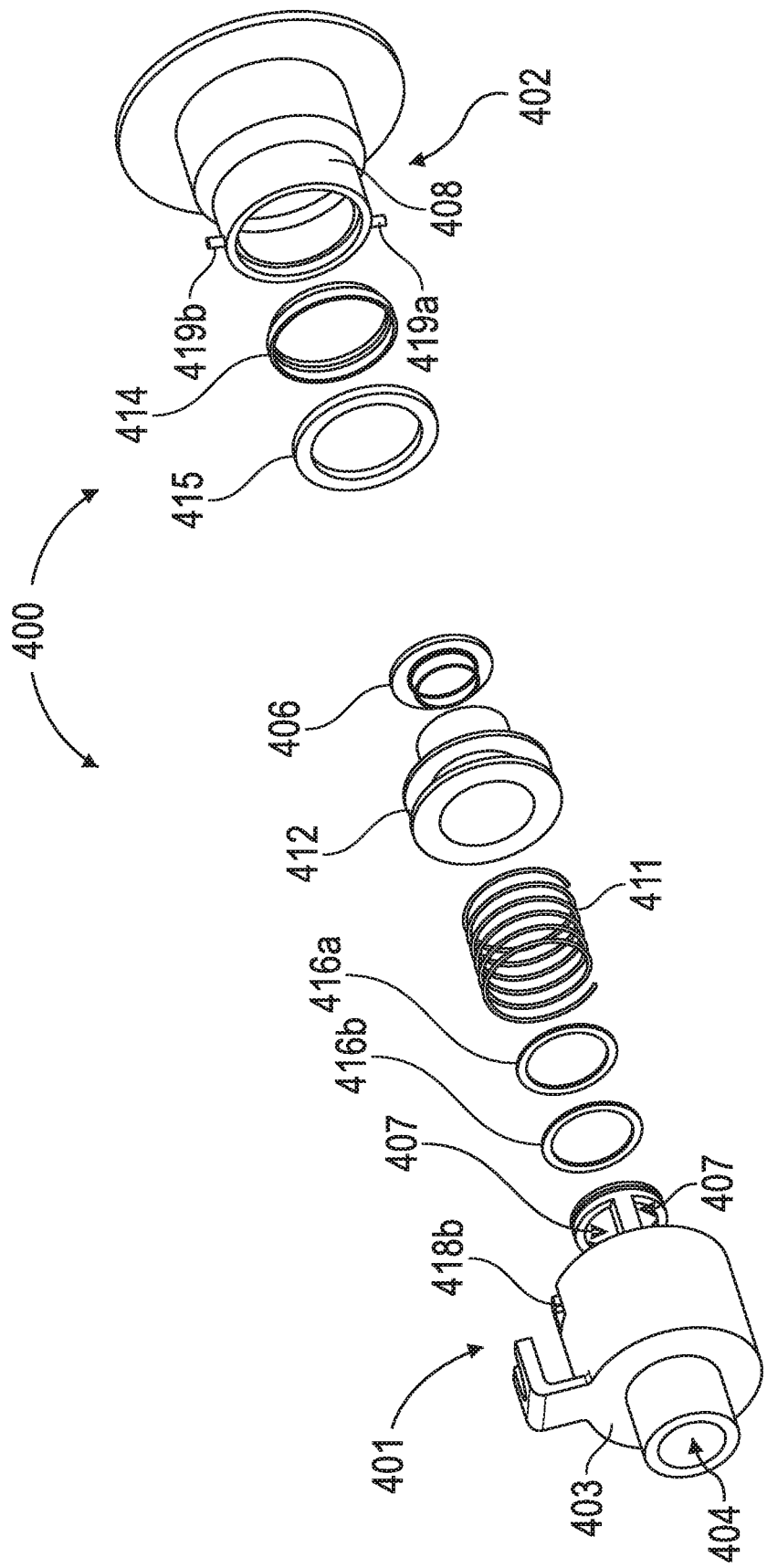
FIG. 14 illustrates an exploded view of the bag connector system of FIG. 12.

Referring to FIGS. 12 and 13, in the uncoupled state of the bag connector system 400, the sliding cover 412 completely covers the openings 407 of the housing 403, creating a seal by interacting with O-rings 416a and 416b located on housing 403 at the distal and proximal ends of the openings 407. The O-rings 416a and 416b may be made of silicone, rubber, or other elastomer. The duckbill valve 414 is in the closed position, preventing backflow of fluid from housing 408.

Figure 15:
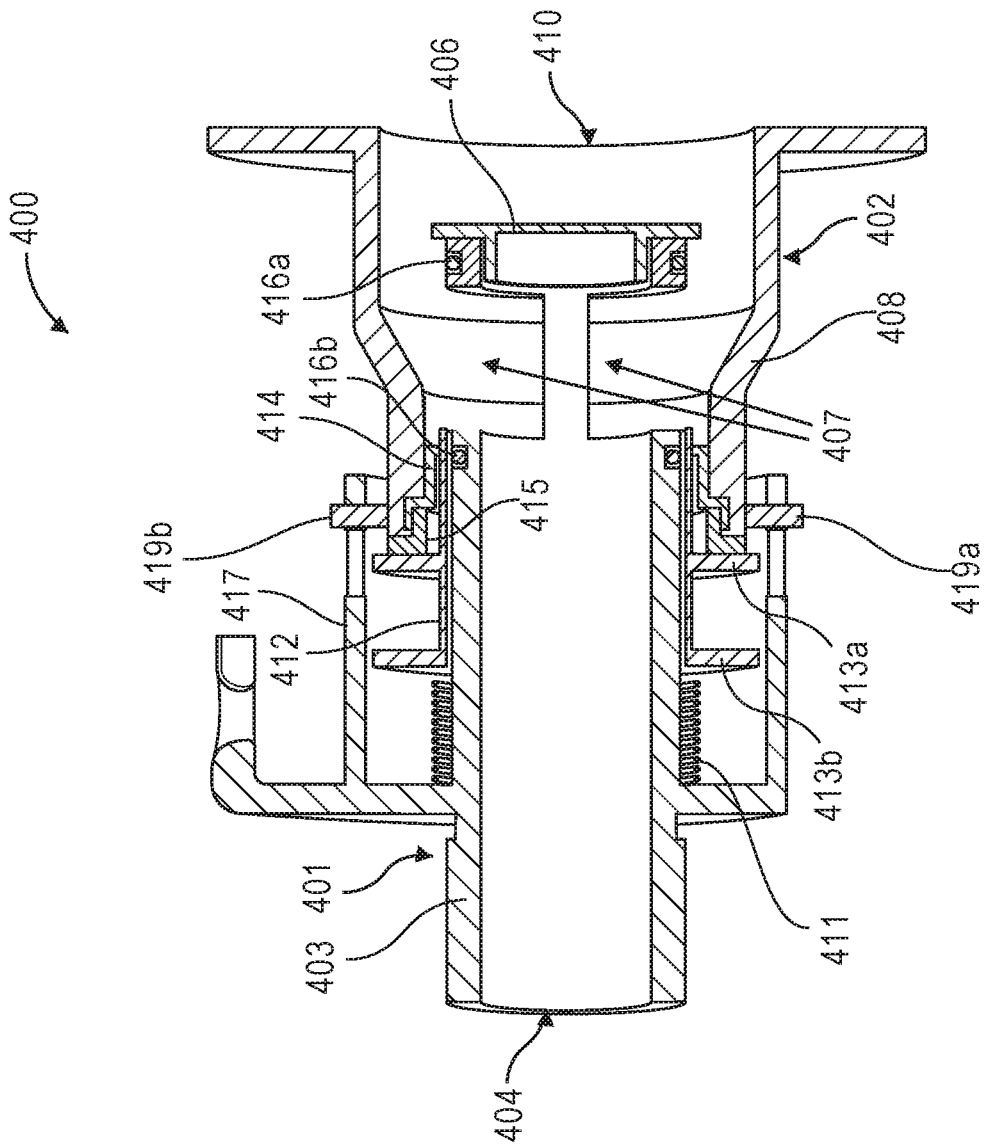
FIG. 15 illustrates a schematic cross-sectional view of the bag connector system of FIG. 12; in this particular figure, the coupling elements are coupled and the bag connector system is in the coupled state.

Referring to FIG. 15, in the coupled state of the bag connector system 400, the valve holder 415 is pushed against the flange 413a of the sliding cover 412, until the flange 413b compresses the spring element 411 and the valve holder 415 has entered the fluid outlet port 405. In a modified embodiment, the valve holder 415 is pushed against the flange 416 of the sliding cover 412, until the flange 413b also compresses the spring element 411.

The movement of the sliding cover 412 provides partial or complete exposure of the openings 407. Concomitantly, the cap 406 is pushed against the duckbill valve 414, partially or fully opening this valve and situating the partial or completely exposed openings 407 to be within the housing 408. Fluid within the housing 403 can now flow directly through openings 407 and into housing 408.

Each of the first coupling element 401 and the second coupling element 402 further comprises complementary components of a locking mechanism, which maintains the first coupling element and the second coupling element in a coupled state. Such locking mechanisms include a twist lock-in mechanism, bayonet latch, or other locking mechanism which maintains a coupled state between the first coupling element and the second coupling element. For example, in one embodiment, the first coupling element 401 comprises at least one of the complementary components of a locking mechanism. The external edge of the fluid outlet port 405 is a rotatable locking member 417 having two slots 418a and 418b which receive pins 419a and 419b located on the outer surface of the fluid inlet end 409. When the twist lock-in mechanism is in a first position, the pins 419a and 419b can pass through the complementary slots 418a and 418b, easily coupling or uncoupling the first coupling element 401 and the second coupling element 402. When the twist lock-in mechanism is in a second position, the pins 419a and 419b cannot pass through the complementary slots 418a and 418b, maintaining the first coupling element 401 and the second coupling element 402 in a coupled state. The twist lock-in mechanism is toggled between the first and second positions by rotating the coupled coupling elements in opposing directions along the axis of the fluid flow pathway.

To uncouple the first coupling element 401 and the second coupling element 402, the twist lock-in mechanism is toggled to the first position and the two coupling elements 401 and 402 are pulled in opposing directions away from each other. The spring element 411 pushes the sliding cover 412 to once again fully cover the openings 407. The duckbill valve 414 also self-seals upon uncoupling of the first coupling element 401 and the second coupling element 402.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A bag connector system, comprising:
   a first coupling element, comprising:
      a first housing having a first fluid inlet and a first fluid outlet; and
      a self-closing seal to prevent fluid flow from exiting the first fluid outlet, wherein the self-closing seal comprises a sliding cover connected to a spring element; and
   a second coupling element, comprising:
      a second housing having a second fluid inlet and a second fluid outlet, the second coupling element fluid inlet configured to displace the self-closing seal when engaged with the first fluid outlet;
      a check valve; and
      a valve holder positioned about the second fluid inlet and retaining at least a portion of the check valve in a fixed position.

2. The bag connector system of claim 1, wherein the check valve comprises a duckbill valve.

3. The bag connector system of claim 1, wherein the first coupling element further comprises at least one O-ring.

4. The bag connector system of claim 1, further comprising means to maintain the first coupling element and the second coupling element in a coupled state.

5. The bag connector system of claim 4, wherein the means to maintain the first coupling element and the second coupling element in the coupled state comprises at least one of a twist lock-in mechanism, a single cantilever snap-fit mechanism, a multiple cantilever snap-fit mechanism, an annular snap-fit mechanism, or an interference fit mechanism.

6. The bag connector system of claim 1, wherein upon disconnection of the first coupling element and the second coupling element, the spring element pushes the sliding cover into position to close a drainage path.

7. A medical appliance for managing fecal or urinary waste comprising the bag connector system of claim 1, and further comprising an external waste storage container.

8. A bag connector system, comprising:
a first coupling element, comprising:
a first housing having a first end portion and a second end portion, wherein the first end portion includes a first fluid port, wherein the second end portion includes a second fluid port; and
a slidable cover movably mounted to the first housing and operable to selectively cover the second fluid port; and
a second coupling element, the second coupling element comprising:
a second housing having a third fluid port and a fourth fluid port, wherein the third fluid port is sized and shaped to engage the second end portion of the first housing;
a self-closing seal disposed in the third fluid port; and
a collar mounted to the second housing and maintaining a portion of the self-closing seal in a fixed position.

9. The bag connector system of claim 8, wherein the second housing is configured to open the slidable cover during engagement of the second end portion with the third fluid port; and
wherein the second end portion of the first housing is configured to open the self-closing seal during engagement of the second end portion with the third fluid port.

10. The bag connector system of claim 8, further comprising a lock mechanism operable to maintain the first coupling element and the second coupling element in a coupled state, wherein lock mechanism comprises at least one of an interference fit mechanism, a twist lock-in mechanism, or a snap-fit mechanism.

11. The bag connector system of claim 8, wherein the self-closing seal comprises means for biasing the self-closing seal toward a closed state.

12. The bag connector system of claim 8, wherein the self-closing seal comprises a check valve.

13. The bag connector system of claim 8, further comprising a biasing element urging the slidable cover toward a closed position.

14. The bag connector system of claim 8, further comprising an O-ring forming a seal between the second end portion and the slidable cover when the slidable cover is closed.

15. The bag connector system of claim 8, further comprising a pair of O-rings positioned on opposite sides of the second fluid port and configured to form seals between the second end portion and the slidable cover when the slidable cover is closed.

16. A bag connector system, comprising:
a first coupling element, comprising:
a first housing having a first end portion and a second end portion, wherein the first end portion includes a first fluid port, wherein the second end portion includes a second fluid port formed in an outer periphery thereof and a solid end wall; and
a cover sleeve slidably mounted to the second end portion for movement between a closed position in which the cover sleeve covers the second fluid port and an open position in which the cover sleeve exposes at least a portion of the second fluid port; and
a second coupling element, comprising:
a second housing having a third fluid port and a fourth fluid port, wherein the third fluid port is sized and shaped to engage the second end portion of the first housing; and
a self-closing seal disposed in the third fluid port, the self-closing seal having an open state and a closed state, wherein the self-closing seal is biased toward the closed state;
wherein the self-closing seal comprises:
a perforated plate disposed within the second housing;
a solid plate having a first position in which the solid plate seals the third fluid port and a second position in which the solid plate is nearer the perforated plate; and
a spring engaged between the perforated plate and the solid plate and biasing the solid plate toward the first position.

17. The bag connector system of claim 16, wherein the first coupling element further comprises a first coupler; and
wherein the second coupling element further comprises a second coupler configured to engage the first coupler to retain the bag connector system in a coupled state in which the second end portion is engaged with the third fluid port, the cover sleeve is in the open position, and the self-closing seal is in the open state.

18. The bag connector system of claim 17, further comprising means for retaining the bag connector system in the coupled state, the means for retaining including the first coupler and the second coupler.

19. The bag connector system of claim 16, wherein the second housing is configured to move the cover sleeve from the closed position to the open position during engagement of the second end portion with the third fluid port; and
wherein the second end portion of the first housing is configured to move the self-closing seal from the closed state to the open state during engagement of the second end portion with the third fluid port.

20. The bag connector system of claim 16, further comprising a pair of O-rings positioned on opposite sides of the second fluid port, the pair of O-rings forming a pair of seals between the first housing and the cover sleeve when the cover sleeve is in the closed position; and
wherein one of the O-rings forms a seal between the first housing and the cover sleeve when the cover sleeve is in the open position.

* * * * *